(12) United States Patent
Warrell et al.

(10) Patent No.: US 7,795,232 B1
(45) Date of Patent: Sep. 14, 2010

(54) METHODS OF TREATMENT OF A BCL-2 DISORDER USING BCL-2 ANTISENSE OLIGOMERS

(75) Inventors: Raymond P. Warrell, Berkeley Heights, NJ (US); Robert E. Klem, Berkeley Heights, NJ (US); Howard Fingert, Berkeley Heights, NJ (US)

(73) Assignee: Genta Incorporated, Berkeley Heights, NJ (US)

( * ) Notice: Subject to any disclaimer, the term of this patent is extended or adjusted under 35 U.S.C. 154(b) by 368 days.

(21) Appl. No.: 09/709,170

(22) Filed: Nov. 10, 2000

Related U.S. Application Data

(60) Provisional application No. 60/227,970, filed on Aug. 25, 2000, provisional application No. 60/237,009, filed on Sep. 29, 2000.

(51) Int. Cl.
*A01N 43/04* (2006.01)
*A61K 31/70* (2006.01)
*C07H 21/02* (2006.01)
*C07H 21/04* (2006.01)

(52) U.S. Cl. ............... 514/44; 536/23.1; 536/24.3; 536/24.33; 536/24.5

(58) Field of Classification Search ............. 435/6, 435/375, 325, 91.1; 514/44; 536/23.1, 24.5, 536/24.1, 24.3
See application file for complete search history.

(56) References Cited

U.S. PATENT DOCUMENTS

| | | | |
|---|---|---|---|
| 5,098,890 A | 3/1992 | Gewirtz et al. | |
| 5,202,429 A | 4/1993 | Tsujimoto et al. | |
| 5,459,251 A | 10/1995 | Tsujimoto et al. | |
| 5,734,033 A | 3/1998 | Reed | |

(Continued)

FOREIGN PATENT DOCUMENTS

EP 88302617 3/1988

(Continued)

OTHER PUBLICATIONS

Fl Raynaud et al. Journal of Pharmacology and Experimental Therapeutics,"Pharmacokinetics of G3139, a Phosphorothioate Oligodeoxynucleotide . . . Intravenous Administration or Continuous Subcutaneous Infusion to Mice," Dec. 1996,vol. 281,No. 1,pp. 420-427.*

(Continued)

*Primary Examiner*—Fereydoun Sajjadi
*Assistant Examiner*—Terra Cotta Gibbs
(74) *Attorney, Agent, or Firm*—Diehl Servilla LLC

(57) ABSTRACT

The present invention is directed to the use of bcl-2 antisense oligomers to treat and prevent bcl-2 related disorders. These disorders include cancers, tumors, carcinomas and cell-proliferative related disorders. In one embodiment of the invention, a bcl-2 antisense oligomer is administered at high doses. The present invention is also directed to a method of preventing or treating a bcl-2 related disorder, in particular cancer, comprising administering a bcl-2 antisense oligomer for short periods of time. The present invention is further drawn to the use of bcl-2 antisense oligomers to increase the sensitivity of a subject to cancer therapeutics. The present invention also relates to pharmaceutical compositions comprising one or more bcl-2 antisense oligomers, which may comprise one or more cancer therapeutic agents.

14 Claims, 3 Drawing Sheets

Actin

Bcl-2 day 0    day 5

U.S. PATENT DOCUMENTS

Figure 1:
Figure 1:

| | | | |
|---|---|---|---|
| 5,831,066 A | 11/1998 | Reed | |
| 6,040,181 A | 3/2000 | Reed | |
| 6,214,986 B1 * | 4/2001 | Bennett et al. | 536/24.5 |

FOREIGN PATENT DOCUMENTS

| | | |
|---|---|---|
| WO | WO 91/04014 | 4/1991 |
| WO | WO 93/20200 | 10/1993 |
| WO | WO 94/08625 | 4/1994 |
| WO | WO 94/27426 | 12/1994 |

OTHER PUBLICATIONS

DE Lopes de Menezes et al., Clinical Cancer Res.,"Molecular and Pharmacokinetic Properties Associated with the Therapeutics of Bcl-2 . . . Rree and Liposomal Doxorubicin," Jul. 2000, vol. 6, pp. 2891-2902.*
H Miayake et al., Journal of the Natl.Cancer institute,"Chemosensitization and Delayed Androgen-Independent Recurrence . . . Antisense Bcl-2 Oligodeoxynucleotides,"Jan. 2000, vol. 92, No. 1, pp. 34-41.*
FE Cotter et al., Biochimica et BiophysicaActa 1489,"Human Bcl-s antisense therapy for lymphomas," 1999, pp. 97-106.*
A Webb et al., The Lancet, "BCL-2 antisense therapy in patients with non-Hodgkin lymphoma," Apr. 1997, vol. 349, pp. 1137-1141.*
JS Waters et al., Journal of Clinical Oncology, "Phase I Clinical and Pharmacokinetic Study of Bcl-2 Antisense Oligonucleotide Therapy in Patients with Non-Hodgkin's Lymphoma," May 2000, vol. 18, No. 9, pp. 1812-1823.*
W Tong et al., American Society of Clinical Oncology,"Phase I/IIA Dose-Escalating Trial of bcl-2 Antisense (G3139) Treatment by 14-Day Continuous . . . Solid Tumor Malignancies," 1999, Abstract.*
BJansen et al.,American Society of Clinical Oncology,"Phase I-II Study with Dacarbazine and BCL-2 Antisense Oligonucleotide G3139(GENTA) . . . Advanced Malignant Melanoma," 1999, Abstract.*
B Jansen et al.,The Lancet, "Chemosensitisation of malignant melanoma by BCLa antisense therapy," Nov. 2000, vol. 356, pp. 1728-1733.*
Webb et al. Bcl-2 antisense therapy in patients with non-Hodgkin lymphoma. The Lancet, 1997 vol. 349:1137-1141.*
Jansen, B. A Phase I-II Study with Dacarbazine and bcl-2 antisense oligonucleotide G3139 (GENTA) as a chemosensitizer in patients with advanced malignant melanoma. American Society of Clinical Oncology, 1999 Abstract.*
Klasa et al. Eradication of Human Non-Hodkin's Lymphoma in SCID mice by Bcl-2 antisense Oligonucleotides combined with lose-dose cyclophosphamide. Clinical Cancer Research, 2000 vol. 6:2492-2500.*
Tortora et al. Cooperative antitumor effect of mixed backbone oligonucleotides targeting protein kinase A in combination with cytotoxic drugs or biologic agents. Antisense and Nucleic acid Drug Development, 1998 vol. 8:141-145.*
Adjei et al. Docetaxel and Irinotecan, Alone and in combination, in the treatment of non-small cell lung cancer. Seminars in Oncology, 1999 vol. 26:32-40.*
Foran et al. Multicenter Phase II Study of Fludarabine Phosphate for Patients with Newly Diagnosed lymphoplasmacytoid and Mantle-cell lymphoma. Journal of Clinical Oncology, 1999 vol. 17:546-553.*
Murren et al. Dose escalation and pharmacokinetic study of irinotecan in combination with paclitaxel patients with advanced cancer. Caner Chemotherapy Pharmacology, 2000 vol. 46:43-50.*
Asseline et al, Nucleic acid-binding molecules with high affinity and base sequence specificity: intercalating agents covalently linked to oligodeoxynucleotides. Proc Natl Acad Sci Jun. 1984;81(11):3297-301.
Bishop JM. The molecular genetics of cancer. Science. Jan. 16, 1987;235(4786):305-11.
Blake et al, Inhibition of rabbit globin mRNA translation by sequence-specific oligodeoxyribonucleotides. Biochemistry. Oct. 22, 1985;24(22):6132-8.

Boutorin et al., Synthesis of alkylating oligonucleotide derivatives containing cholesterol or phenazinium residues at their 3'-terminus and their interaction with DNA within mammalian cells. FEBS Lett. Aug. 28, 1989;254(1-2):129-32.
Bronner et al., Bcl-2 protooncogene and the gastrointestinal mucosal epithelial tumor progression model as related to proposed morphologic and molecular sequences. Lab. Invest. 1993, 68:43A.
Brooks et al., Requirement of vascular integrin alpha v beta 3 for angiogenesis. Science. Apr. 22, 1994;264(5158):569-71.
Buchwald et al., Long-term, continuous intravenous heparin administration by an implantable infusion pump in ambulatory patients with recurrent venous thrombosis. Surgery. Oct. 1980;88(4):507-16.
Campos et al.,"High expression of bcl-2 protein in acute myeloid leukemia is associated with poor response to chemotherapy." Blood 1993, 81:3091-6.
*Cancer: Principles & Practice of Oncology*, DeVita, Jr., Hellman and Rosenberg (eds.) $2^{nd}$ edition, Pheladelphia, PA :J.B. Lippincott Co., 1985.
Cao, Endogenous angiogenesis inhibitors: angiostatin, endostatin, and other proteolytic fragments. Prog Mol Subcell Biol. 1998, 20:161-76.
Chapman et al., Phase III multicenter randomized trial of the Dartmouth reimen versus dacarbazine in patients with metastatic melanoma. J. Clin. Oncol. 1999, 17(9):2745-51.
Chen et al., Determination of N(G),N(G)-dimethylarginine in human plasma by high-performance liquid chromatography. J Chromatogr B Biomed Sci Appl. May 9, 1997; 692(2):467-71.
Chi-Hong et al., Nuclease activity of 1,10-phenanthroline-copper: sequence-specific targeting. Proc Natl Acad Sci Oct. 1986;83(19):7147-51.
Chu et al., Nonenzymatic sequence-specific cleavage of single-stranded DNA. Proc Natl Acad Sci. Feb. 1985;82(4):963-7.
*Controlled Drug Bioavailability, Drug Product Design and Performance*, Smolen and Ball (eds.), Wiley: New York (1984).
Cotter et al., Antisense oligonucleotides suppress B-cell lymphoma growth in a SCID-hu mouse model. Oncogene. Oct. 1994;9(10):3049-55.
Croce et al., Molecular basis of human B and T cell neoplasia. *Advance in Viral Oncology*, G. Klein(ed.), New York, Raven Press. 1987, 7:35-51.
Crowley et al., Prevention of metastasis by inhibition of the urokinase receptor. Proc Natl Acad Sci, Jun. 1, 1993;90(11):5021-5.
Egholm et al., 1992, *Peptide Nucleic Acids (PNA)-Oligonucleotide Analogues With an Achiral Peptide Backbone*. J.Am. Chem.Soc 1992, 114:1895-97.
Goodchild, Conjugates of oligonucleotides and modified oligonucleotides: a review of their synthesis and properties, Bioconjug. Chem. 1990, 1(3):165-87.
Goodson, 1984, "Dental Applications" in *Medical Applications of Controlled Release*, vol. 2, pp. 115-138.
Grover et al., Bcl-2 expression in malignant melanoma and its prognostic significance Eur. J. Surg. Oncol. 1996, 22(4):347-9.
Halder et al., The bcl-2 gene encodes a novel G protein. Nature. Nov. 9, 1989;342(6246):195-8.
Holt, et al., An oligomer complementary to c-myc mRNA inhibits proliferation of HL-60 promyelocytic cells and induces differentiation. Mol Cell Biol. Feb. 1988;8(2):963-73.
Jansen et al., "Bcl-2 antisense therapy chemosensitizes human melanoma in SCID mice" Nat. Med. 1998, 4(2):232-4.
Kitada et al., Reversal of chemoresistance of lymphoma cells by antisense-mediated reduction of bcl-2 gene expression. Antisense Res Dev. 1994 Summer;4(2):71-9.
Kitada et al., Investigations of antisense oligonucleotides targeted against bcl-2 RNAs. Antisense Res Dev. 1993 Summer;3(2):157-69.
Knorre et al., Reactive oligonucleotide derivatives and sequence-specific modification of nucleic acids. Biochimie. Jul.-Aug. 1985;67(7-8):785-9.
Langer and Peppas, 1981 "Present and Future Applications of Biomaterials in Controlled Drug Delivery Systems", J. Biomaterials 2(3):201-14.
Langer, New methods of drug delivery. Science. Sep. 28, 1990;249(4976):1527-33.

Lu et al., "Bcl-2 protooncogene expression in Epstein Barr Virus-associated nasopharyngeal carcinoma." Int. J. Cancer 1993, 53:29-35.

McDonnell et al., Expression of the protooncogene bcl-2 and its association with emergence of androgen-independent prostate cancer. Cancer Res. 1992, 52:6940-4.

Min et al., Urokinase receptor antagonists inhibit angiogenesis and primary tumor growth in syngeneic mice. Cancer Res. May 15, 1996;56(10):2428-33.

Miyashita et al., bcl-2 gene transfer increases relative resistance of S49.1 and WEHI7.2 lymphoid cells to cell death and DNA fragmentation induced by glucocorticoids and multiple chemotherapeutic drugs. Cancer Res. Oct. 1, 1992;52(19):5407-11.

Miyashita et al., Bcl-2 oncoprotein blocks chemotherapy-induced apoptosis in a human leukemia cell line. Blood. Jan. 1, 1993;81(1):151-7.

Monia et al., Evaluation of 2'-modified oligonucleotides containing 2' deoxy gaps as antisense inhibitors of gene expression, J. Biol. Chem. 1993, 268:14514-22.

Morvan et al., alpha-DNA. I. Synthesis, characterization by high field 1H-NMR, and base-pairing properties of the unnatural hexadeoxyribonucleotide alpha-[d(CpCpTpTpCpC)] with its complement beta-[d(GpGpApApGpG)]. Nucleic Acids Res. Jun. 25, 1986;14(12):5019-35.

Negrini et al., Molecular analysis of mbcl-2: structure and expression of the murine gene homologous to the human gene involved in follicular lymphoma. Cell. May 22, 1987;49(4):455-63.

Paoletti C. Anti-sense oligonucleotides as potential antitumour agents: prospective views and preliminary results. Anticancer Drug Des. Mar. 1988;2(4):325-31.

*Physicians' Desk Reference*, 54th Edition (2000).

Raynaud et al., Pharmacokinetics of G3139, a phosphorothioate oligodeoxynucleotide antisense to bcl-2, after intravenous administration or continuous subcutaneous infusion to mice. J Pharmacol Exp Ther. Apr. 1997;281(1):420-7.

Reed, Regulation of apoptosis by bcl-2 family proteins and its role in cancer and chemoresistance Curr. Opin. Oncol. 1995, 7:541-6.

Reed et al., Regulation of chemoresistance by the bcl-2 oncoprotein in non-Hodgkin's lymphoma and lymphocytic leukemia cell lines. Ann Oncol. 1994;5 Suppl 1:61-5.

Reed et al., Antisense-mediated inhibition of BCL2 protooncogene expression and leukemic cell growth and survival: comparisons of phosphodiester and phosphorothioate oligodeoxynucleotides. Cancer Res. Oct. 15, 1990;50(20):6565-70.

Reed et al., "Differential expression of bcl-2 protooncogene in neuroblastoma and other human tumor cell lines of neural origin." Cancer Res. 1991 51:6529-38.

Reed et al., BCL2-mediated tumorigenicity of a human T-lymphoid cell line: synergy with MYC and inhibition by BCL2 antisense. Proc Natl Acad Sci May 1990;87(10):3660-4.

Reed et al., Regulation of bcl-2 proto-oncogene expression during normal human lymphocyte proliferation. Science. Jun. 5, 1987;236(4806):1295-9.

Selzer et al., Expression of Bcl-2 family members in human melanocytes, in melanoma metastases and in melanoma cell lines. Melanoma Res. Jun. 1998;8(3):197-203.

Stein et al., Oligodeoxynucleotides as inhibitors of gene expression: a review. Cancer Res. May 15, 1988;48(10):2659-68.

Stein et al., Physicochemical properties of phosphorothioate oligodeoxynucleotides. Nucleic Acids Res. Apr. 25, 1988;16(8):3209-21.

Strasser et al., bcl-2 transgene inhibits T cell death and perturbs thymic self-censorship. Cell. Nov 29, 1991;67(5):889-99.

Stull et al., Antigene, ribozyme and aptamer nucleic acid drugs: progress and prospects. Pharm Res. Apr. 1995;12(4):465-83.

Treat et al., 1989, "Liposome Encapsulated Doxorubicin Preliminary Results of Phase I and Phase II Trials" in *Liposomes in the Therapy of Infectious Disease and Cancer*, Lopez-Berestein and Fidler (eds.), Liss, New York, pp. 353-365.

Tsujimoto et al., Involvement of the bcl-2 gene in human follicular lymphoma. Science 1985, 228:1440-1443.

Uhlmann et al., EMD 53998 acts as Ca(2+)-sensitizer and phosphodiesterase III-inhibitor in human myocardium. Basic Res Cardiol. Sep.-Oct. 1995;90(5):365-71.

Vlassov et al., Complementary addressed modification and cleavage of a single stranded DNA fragment with alkylating oligonucleotide derivatives. Nucleic Acids Res. May 27, 1986;14(10):4065-76.

Waters et al., Phase I clinical and pharmacokinetic study of bcl-2 antisense oligonucleotide therapy in patients with non-Hodgkin's lymphoma. J Clin Oncol. May 2000;18(9):1812-23.

Webb et al., BCL-2 antisense therapy in patients with non-Hodgkin lymphoma. Lancet. Apr. 19, 1997;349(9059):1137-41.

Webb et al., Hybridization triggered cross-linking of deoxyoligonucleotides. Nucleic Acids Res. Oct. 10, 1986;14(19):7661-74.

Wickstrom et al., Human promyelocytic leukemia HL-60 cell proliferation and c-myc protein expression are inhibited by an antisense pentadecadeoxynucleotide targeted against c-myc mRNA. Proc Natl Acad Sci Feb. 1988;85(4):1028-32.

Williams, Programmed cell death: apoptosis and oncogenesis. Cell. Jun. 28, 1991;65(7):1097-8.

Yunis et al., Bcl-2 and other genomic alterations in the prognosis of large-cell lymphomas. N. Engl. J. Med. 1989, 320:1047-54.

Zamecnik et al., Inhibition of replication and expression of human T-cell lymphotropic virus type III in cultured cells by exogenous synthetic oligonucleotides complementary to viral RNA. Proc Natl Acad Sci Jun. 1986;83(12):4143-6.

Zamecnik and Stephenson, Inhibition of Rous sarcoma virus replication and cell transformation by a specific oligodeoxynucleotide. Proc Natl Acad Sci Jan. 1978;75(1):280-4.

* cited by examiner day 0      day 5

METHODS OF TREATMENT OF A BCL-2 DISORDER USING BCL-2 ANTISENSE OLIGOMERS

This application claims the benefit of U.S. Patent Application Ser. No. 60/227,970, filed Aug. 25, 2000 and U.S. Patent Application Ser. No. 60/237,009, filed Sep. 29, 2000.

1. INTRODUCTION

The present invention is directed to the use of bcl-2 antisense oligomers to treat and prevent bcl-2 related disorders. These disorders include cancers, tumors, carcinomas and cell-proliferative related disorders. In one embodiment of the invention, a bcl-2 antisense oligomer is administered at high doses. The present invention is also directed to a method of preventing or treating a bcl-2 related disorder, in particular cancer, comprising administering a bcl-2 antisense oligomer for short periods of time. The present invention is further drawn to the use of bcl-2 antisense oligomers to increase the sensitivity of a subject to cancer therapeutics. The present invention also relates to pharmaceutical compositions comprising one or more bcl-2 antisense oligomers, which may comprise one or more cancer therapeutic agents.

2. BACKGROUND OF THE INVENTION

Traditional approaches to cancer treatment suffer from a lack of specificity. Most drugs that have been developed are natural products or derivatives which block enzyme pathways or randomly interact with DNA. Moreover, most cancer treatment drugs are accompanied by serious dose-limiting toxicities due to low therapeutic indices. For example, the majority of anti-cancer drugs when administered to a patient kill not only cancer cells but also normal, non-cancerous cells. Because of these deleterious effects, treatments that more specifically affect cancerous cells are needed.

It has been found that a class of genes, the oncogenes, are involved in the transformation of cells, and in the maintenance of a cancerous state. Notably, disrupting the transcription of these genes, or otherwise inhibiting the effects of their protein products, can have a favorable therapeutic result. The role of oncogenes in the etiology of many human cancers has been reviewed in Bishop, 1987, "Cellular Oncogenes and Retroviruses," Science, 235:305-311. In many types of human cancers, a gene termed bcl-2 (B cell lymphoma/leukemia-2) is overexpressed, and this overexpression may be associated with tumorigenicity (Tsujimoto et al., 1985, "Involvement of the bcl-2 gene in human follicular lymphoma", Science 228:1440-1443). The bcl-2 gene is thought to contribute to the pathogenesis of cancer, as well as to resistance to treatment, primarily by prolonging cell survival rather than by accelerating cell division.

The human bcl-2 gene is implicated in the etiology of certain leukemias, lymphoid tumors, lymphomas, neuroblastomas, and nasopharyngeal, prostate, breast, and colon carcinomas (Croce et al., 1987, "Molecular Basis Of Human B and T Cell Neoplasia," in: *Advance in Viral Oncology,* 7:35-51, G. Klein (ed.), New York: Raven Press; Reed et al., 1991, "Differential expression of bcl-2 protooncogene in neuroblastoma and other human tumor cell lines of neural origin", Cancer Res. 51:6529-38; Yunis et al., 1989, "Bcl-2 and other genomic alterations in the prognosis of large-cell lymphomas", N. Engl. J. Med. 320:1047-54; Campos et al., 1993, "High expression of bcl-2 protein in acute myeloid leukemia is associated with poor response to chemotherapy", Blood 81:3091-6; McDonnell et al., 1992, "Expression of the protooncogene bcl-2 and its association with emergence of androgen-independent prostate cancer", Cancer Res. 52:6940-4; Lu et al., 1993, "Bcl-2 protooncogene expression in Epstein Barr Virus-Associated Nasopharyngeal Carcinoma", Int. J. Cancer 53:29-35; Bonner et al., 1993, "bcl-2 protooncogene and the gastrointestinal mucosal epithelial tumor progression model as related to proposed morphologic and molecular sequences", Lab. Invest. 68:43 A). Bcl-2 has been found to be overexpressed in a variety of tumors including non-Hodgkin's lymphoma, lung cancer, breast cancer, colorectal cancer, prostate cancer, renal cancer and acute and chronic leukemias (Reed, 1995, "Regulation of apoptosis by bcl-2 family proteins and its role in cancer and chemoresistance", Curr. Opin. Oncol. 7:541-6).

Antisense oligonucleotides provide potential therapeutic tools for specific disruption of oncogene function. These short (usually less than 30 bases) single-stranded synthetic DNAs have a sequence complementary to pre-mRNA or mRNA regions of a target gene, and form a hybrid duplex by hydrogen-bonded base pairing. This hybridization can disrupt expression of both the target mRNA and the protein which it encodes, and thus can interfere with downstream interactions and signaling. Since one mRNA molecule gives rise to multiple protein copies, inhibition of the mRNA can be more efficient and more specific than causing disruption at the protein level, e.g., by inhibition of an enzyme's active site.

Synthetic oligodeoxynucleotides complementary to mRNA of the c-myc oncogene have been used to specifically inhibit production of c-myc protein, thereby arresting the growth of human leukemic cells in vitro (Holt et al., 1988, Mol. Cell Biol. 8:963-73; Wickstrom et al., 1988, Proc. Natl. Acad. Sci. USA, 85:1028-32). Oligodeoxynucleotides have also been employed as specific inhibitors of retroviruses, including the human immunodeficiency virus (Zamecnik and Stephenson, 1978, Proc. Natl. Acad. Sci. USA, 75:280-4; Zamecnik et al., 1986, Proc. Natl. Acad. Sci. USA, 83:4143-6).

The use of antisense oligonucleotides, with their ability to target and inhibit individual cancer-related genes, has shown promise in preclinical cancer models. These phosphorothioate antisense oligomers have shown an ability to inhibit bcl-2 expression in vitro and to eradicate tumors in mouse models with lymphoma xenografts. Resistance to chemotherapy of some cancers has been linked to expression of the bcl-2 oncogene (Grover et al., 1996, "Bcl-2 expression in malignant melanoma and its prognostic significance", Eur. J. Surg. Oncol. 22(4):347-9). Administration of a bcl-2 antisense oligomer can selectively reduce bcl-2 protein levels in tumor xenografts in laboratory mice (Jansen et al., 1998, "bcl-2 antisense therapy chemosensitizes human melanoma in SCID mice", Nat. Med. 4(2):232-4). Moreover, administration of a bcl-2 antisense oligomer can make tumor xenografts in laboratory mice more susceptible to chemotherapeutic agents (Jansen et al., 1998, "bcl-2 antisense therapy chemosensitizes human melanoma in SCID mice", Nat. Med. 4(2):232-4). In mice, systemic treatment with a bcl-2 antisense oligomer reduced bcl-2 protein and enhanced apoptosis. Treatment with bcl-2 antisense oligomer alone had modest antitumor activity, but enhanced antitumor activity was observed when combined with DTIC (also known as dacarbazine). In ten of thirteen animals, no malignant melanoma xenografts were detectable after administration of bcl-2 antisense oligomer in combination with DTIC treatment. There remains a compelling need to extend these antitumor treatments to combat cancer in humans.

The prognosis of many cancer patients is poor despite the increasing availability of biologic, drug, and combination therapies. For example, although DTIC is commonly used to treat metastatic melanoma, few patients have demonstrated long-term improvement. In fact, an extensive phase III clinical trial did not demonstrate any better survival when DTIC was used in combination with cisplatin, carmustine, and tamoxifen (Chapman et al., 1999, "Phase III multicenter randomized trial of the Dartmouth regimen versus dacarbazine in patients with metastatic melanoma", J. Clin. Oncol. 17(9): 2745-51). These serious shortcomings in cancer treatments emphasize the need for new treatment approaches.

3. SUMMARY OF THE INVENTION

The present invention is directed to pharmaceutical compositions comprising bcl-2 antisense oligomers and methods for treating bcl-2 related disorders. The invention is based, in part, on the Applicants' discovery that a bcl-2 antisense oligomer, when administered to patients at high doses for the treatment of a bcl-2 related disorder, particularly cancer, results in significant therapeutic responses, including low toxicity, high tolerance and prolonged survival. The Applicants also discovered that bcl-2 antisense oligomers, when administered to patients at high doses for a short period of time, i.e., less than 14 days, also resulted in significant therapeutic responses in the treatment of cancer patients. These therapeutic regimens further encompassed administering the bcl-2 antisense oligomer at high doses for the short time in combination with one or more cancer therapeutics. Surprisingly, a reduced dose of one or more cancer therapeutics, when given in combination with the short administration of a bcl-2 antisense oligomer, also demonstrated significant therapeutic responses in the treatment of cancer patients. Thus, the therapeutic regimens of the present invention provide a therapeutically effective method of treating cancer which is of reduced duration and toxicity, and as thus results in improved tolerance.

In one embodiment, the present invention provides a method for treating a bcl-2 related disorder, and a pharmaceutical composition in dosage unit form comprising particularly high doses of a bcl-2 antisense oligomer, such that the effective amount of bcl-2 antisense oligomer in said pharmaceutical composition is a dose effective to achieve a dose of about 10 to 50 mg/kg/day. In accordance with this embodiment of the invention, the effective amount of bcl-2 antisense oligomer of said pharmaceutical composition is a dose effective to achieve a circulating level of bcl-2 antisense oligomer of a minimum of 30 nM (nanomolar). In one embodiment, the circulating level of bcl-2 antisense oligomer is 1 to 10 μM (micromolar). In another embodiment, the desired circulating level of bcl-2 antisense oligomer of at least 30 nM is achieved about 1, 2, 3, 4, 5, 6, 7, 8, 9 or 10 hours after the administration of the bcl-2 antisense oligomer. In another embodiment, the circulating level of bcl-2 antisense oligomer of at least 30 nM is achieved within about 36 to 48 hours, preferably 24 to 35 hours, more preferably in 12 to 24 hours; most preferably in under 12 hours.

In another embodiment, the present invention provides a method for treating a bcl-2 related disorder and a pharmaceutical composition comprising a dose of bcl-2 antisense oligomer to be administered for a short period of time, i.e., less than 14 days, such that the effective amount of bcl-2 antisense oligomer to be administered for the duration of this short treatment cycle ranges from about 0.01 to 50 mg/kg/day. In another embodiment, the effective amount of bcl-2 antisense oligomer to be delivered for the duration of this short treatment cycle is a dose effective to achieve a circulating level of bcl-2 antisense oligomer of a minimum of 30 nM. In another embodiment, the circulating level of bcl-2 antisense oligomer is 1 to 10 (micromolar).

In another embodiment, the present invention provides a method for treating a bcl-2 related disorder and a pharmaceutical composition comprising a dose of bcl-2 antisense oligomer to be administered for a short period of time, i.e., less than 14 days, in combination with one or more cancer therapeutics, said cancer therapeutics to be administered prior to, subsequent to or concurrently with the bcl-2 antisense oligomer. The effective amount of bcl-2 antisense oligomer to be administered for the duration of this short treatment protocol ranges from about 0.01 to 50 mg/kg/day. The effective amount of cancer therapeutics to be administered in combination with a bcl-2 antisense oligomer may be administered at its standard dose, or alternatively, may be administered at a reduced dose. In accordance with this embodiment of the invention, the effective amount of bcl-2 antisense oligomer of said pharmaceutical composition is a dose effective to achieve a circulating level of bcl-2 antisense oligomer of at least 30 nM. In a specific embodiment, the circulating level of bcl-2 antisense oligomer is achieved within about 36 to 48 hours, preferably within about 24 to 35 hours, most preferably under about 24 hours.

In accordance with the present invention, a bcl-2 related disorder encompasses tumors, cancer, carcinomas, and cell-proliferative disorders.

In accordance with the present invention, a short time period encompasses a time period for administering the bcl-2 antisense which is less than 14 days, ranging from 2 to 13 days; preferably ranging from 3 to 9 days, 4 to 7 days, or 5 to 6 days.

In accordance with the present invention, the dose of bcl-2 antisense oligomer to be administered for a short time period ranges from 0.01 to 50 mg/kg/day; preferably at a dose of 4 to 9 mg/kg/day, and more preferably at a dose of 5 to 7 mg/kg/day.

The present invention also encompasses pharmaceutical compositions comprising an effective amount of one or more bcl-2 antisense oligomers to be administered in accordance with the methods of the present invention. Said pharmaceutical compositions encompass a dose of bcl-2 antisense oligomer ranging from 0.01 to 50 mg/kg/day; preferably at a dose of 4 to 9 mg/kg/day, and more preferably at a dose of 5 to 7 mg/kg/day, in combination with a pharmaceutically acceptable carrier. In another embodiment, the pharmaceutical compositions of the present invention also encompass one or more additional cancer therapeutics. Said pharmaceutical compositions are formulated to be delivered as a continuous infusion, or in one or more bolus administrations, or in one or more administrations during a treatment protocol.

In accordance with the present invention, pharmaceutical compositions of the present invention comprising bcl-2 antisense oligomer may be administered separately from pharmaceutical compositions comprising cancer therapeutic agents.

These and other aspects of the present invention will be better appreciated by reference to the following Figures and Detailed Description.

3.1. DEFINITIONS

As used herein, the phrase "bcl-2 related disorder" refers to a disease that involves regulation of the bcl-2 gene, and includes, but is not limited to, diseases involving cells expressing the bcl-2 gene. Such a disorder encompasses diseases involving cells or tissues that express the bcl-2 gene or a bcl-2 related gene, or diseases involving cells or tissues that no longer express the bcl-2 gene, but normally do. Bcl-related disorders include, but are limited to, cell proliferative disorders and pathologies of cells or tissues that are affected by cells that express the bcl-2 gene or a bcl-2 related gene.

As used herein, the term "cancer" describes a disease state in which a carcinogenic agent or agents causes the transformation of a healthy cell into an abnormal cell, which is followed by an invasion of adjacent tissues by these abnormal cells, and which may be followed by lymphatic or blood-borne spread of these abnormal cells to regional lymph nodes and/or distant sites, i.e., metastasis.

As used herein, the term "tumor" or "growth" means increased tissue mass, which includes greater cell numbers as a result of faster cell division and/or slower rates of cell death. Tumors may be malignant or non-malignant cancers.

As used herein, the phrases "treating cancer" and "treatment of cancer" mean to inhibit the replication of cancer cells, inhibit the spread of cancer, decrease tumor size, lessen or reduce the number of cancerous cells in the body, or ameliorate or alleviate the symptoms of the disease caused by the cancer. The treatment is considered therapeutic if there is a decrease in mortality and/or morbidity, or a decrease in disease burden manifest by reduced numbers of malignant cells in the body.

As used herein, the phrases "preventing cancer" and "prevention of cancer" mean to prevent the occurrence or recurrence of the disease state of cancer. As such, a treatment that impedes, inhibits, or interferes with metastasis, tumor growth, or cancer proliferation has preventive activity.

As used herein, the phrase "antisense oligomer" means an antisense oligonucleotide or an analogue or derivative thereof, and refers to a range of chemical species that recognize polynucleotide target sequences through Watson-and-Crick hydrogen bonding interactions with the nucleotide bases of the target sequences. The target sequences may be RNA or DNA, and may be single-stranded or double-stranded. Target molecules include, but are not limited to, pre-mRNA, mRNA, and DNA.

As used herein, the phrase "bcl-2 gene expression" refers to transcription of the bcl-2 gene which produces bcl-2 pre-mRNA, bcl-2 mRNA, and/or bcl-2 protein. As used herein, the term "derivative" refers to any pharmaceutically acceptable homolog, analogue, or fragment corresponding to the pharmaceutical composition of the invention.

As used herein, the phrase "therapeutics" or "therapeutic agents" refer to any molecules, compounds or treatments that assist in the treatment of a disease. As such, a cancer therapeutic is a molecule, compound or treatment protocol that aids in the treatment of tumors or cancer. The treatment protocol includes, but is not limited to, radiation therapy, dietary therapy, physical therapy, and psychological therapy.

As used herein, the phrase "chemoagent" or "anti-cancer agent" or "anti-tumor agent" or "cancer therapeutic" refers to any molecule, compound or treatment that assists in the treatment of tumors or cancer.

As used herein, the phrase "low dose" or "reduced dose" refers to a dose that is below the normally administered range, i.e., below the standard dose as suggested by the *Physicians' Desk Reference*, 54th Edition (2000) or a similar reference. Such a dose can be sufficient to inhibit cell proliferation, or demonstrates ameliorative effects in a human, or demonstrates efficacy with fewer side effects as compared to standard cancer treatments.

Normal dose ranges used for particular therapeutic agents and standard cancer treatments employed for specific diseases can be found in the *Physicians' Desk Reference*, 54th *Edition* (2000) or in *Cancer: Principles & Practice of Oncology*, DeVita, Jr., Hellman, and Rosenberg (eds.) 2nd edition, Philadelphia, Pa.: J.B. Lippincott Co., 1985.

As used herein, the phrase "reduced toxicity" refers to the reduced side effects and toxicities observed in connection with administering antisense oligonucleotides and cancer therapeutics for shorter duration and/or at lower dosages when compared to other treatment protocols and dosage formulations, including the standard treatment protocols and dosage formulations as described in the *Physicians' Desk Reference*, 54th *Edition* (2000) or in *Cancer: Principles & Practice of Oncology*, DeVita, Jr., Hellman, and Rosenberg (eds.) 2nd edition, Philadelphia, Pa.: J.B. Lippincott Co., 1985.

As used herein, the phrase "treatment cycle" or "cycle" refers to a period during which a single therapeutic or sequence of therapeutics is administered. In one embodiment encompassing the use of a high dose of bcl-2 antisense oligomer, in combination with a standard dose of a cancer therapeutic, the preferred period length of time for one treatment cycle is less than 14 days. The present invention contemplates at least one treatment cycle, generally preferably more than one cycle. In some instances, one treatment cycle may be desired, such as, for example, in the case where a significant therapeutic effect is obtained after one treatment cycle.

As used herein, the phrase "pharmaceutically acceptable carrier" refers to a carrier medium that does not interfere with the effectiveness of the biological activity of the active ingredient. Said carrier medium is essentially chemically inert and nontoxic.

As used herein, the phrase "pharmaceutically acceptable" means approved by a regulatory agency of the Federal government or a state government, or listed in the U.S. Pharmacopeia or other generally recognized pharmacopeia for use in animals, and more particularly for use in humans.

As used herein, the term "carrier" refers to a diluent, adjuvant, excipient, or vehicle with which the therapeutic is administered. Such carriers can be sterile liquids, such as saline solutions in water, or oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The carrier, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Examples of suitable pharmaceutical carriers are described in *Remington's Pharmaceutical Sciences* by E. W. Martin. Examples of suitable pharmaceutical carriers are a variety of cationic lipids, including, but not limited to N-(1(2,3-dioleyloxy)propyl)-N, N,N-trimethylammonium chloride (DOTMA) and diolesylphosphotidylethanolamine (DOPE). Liposomes are also suitable carriers for the antisense oligomers of the invention. Such compositions should contain a therapeutically effective amount of the compound, together with a suitable amount of carrier so as to provide the form for proper administration to the patient. The formulation should suit the mode of administration.

As used herein, the phrase "pharmaceutically acceptable salts" refers to salts prepared from pharmaceutically acceptable, essentially nontoxic, acids and bases, including inorganic and organic acids and bases. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

4. BRIEF DESCRIPTION OF THE FIGURES

FIG. 1: Bcl-2 downregulation after 5 days of treatment with Bcl-2 antisense oligomer in melanoma biopsies of patient #12.

Figure 2:
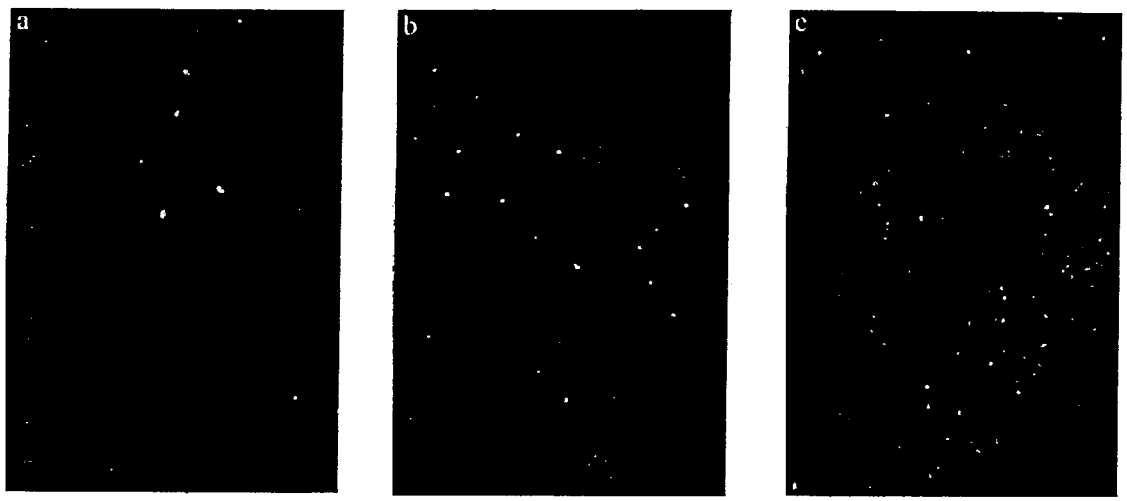

FIG. 2: TUNEL staining of tumor biopsies of patient #12 (right leg) before treatment (a), after Bcl-2 antisense oligomer treatment (b) and after Bcl-2 antisense oligomer plus DTIC treatment.

Figure 3:
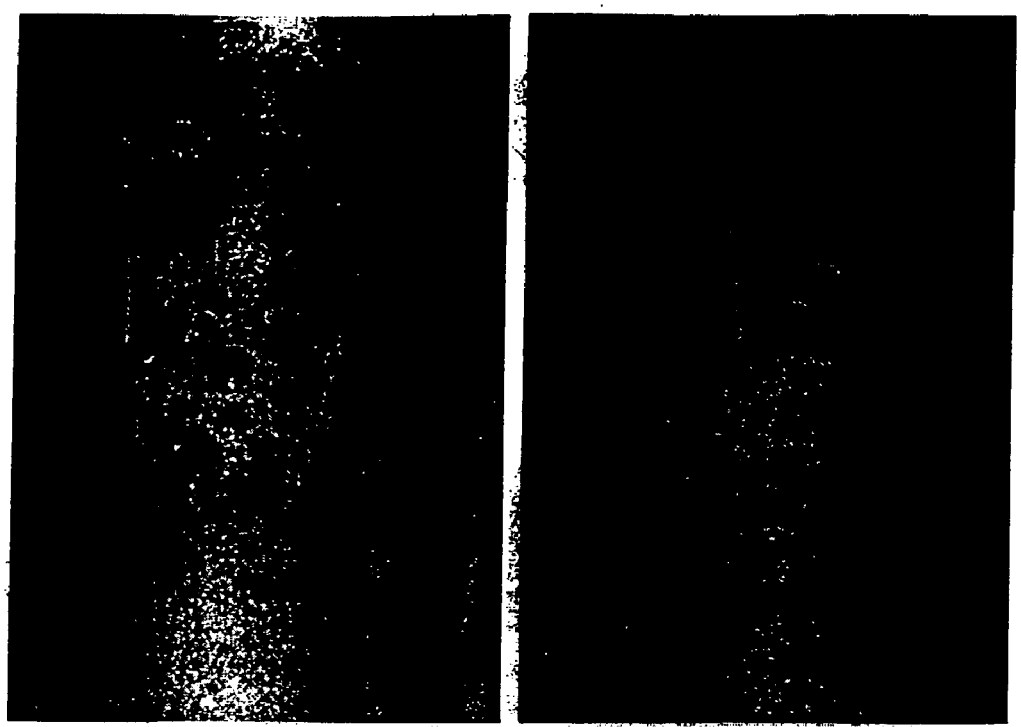
Figure 3:
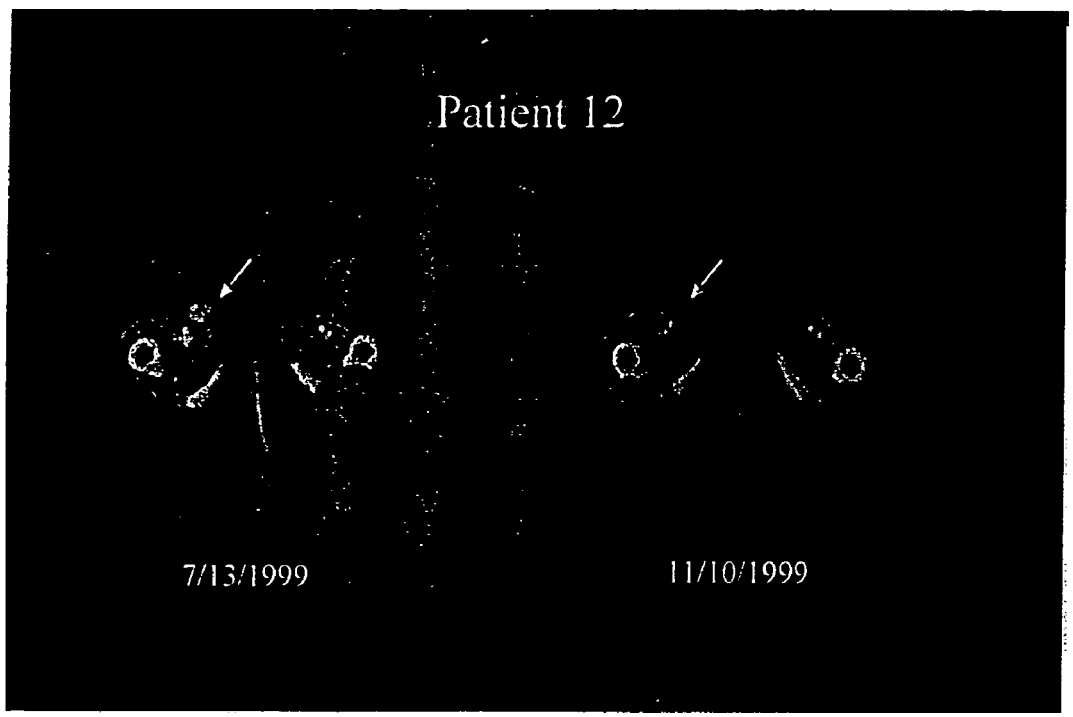

FIG. 3: Skin metastases (a) and CT-scan of pelvic region (b) of patient #12 before and after three cycles of Bcl-2 antisense oligomer plus DTIC treatment at 6.5 mg/kg/day.

5. DETAILED DESCRIPTION OF THE INVENTION

The present invention provides compositions and methods for the use of a bcl-2 antisense oligomer for preventing or treating a bcl-2 related disorder, in particular cancer. The invention also provides pharmaceutical compositions comprising a bcl-2 antisense oligomer, as well as methods for their use in prophylactic and therapeutic treatments, including drug delivery and therapeutic regimens.

The invention is based, in part, on the discovery that short treatment cycles of a bcl-2 antisense oligomer, alone and in combination with other therapeutic agents, has unexpectedly potent ameliorative effects in patients suffering from disease. This short treatment regimen manifests additional benefits to the human subject such as convenience, reduced psychological trauma, and a better likelihood of compliance with the treatment protocol. Other discoveries include: (1) short treatment cycles and reduced doses of therapeutic agents when used in combination with a bcl-2 antisense oligomer, (2) simplified modes of delivery for the pharmaceutical compositions comprising at least one bcl-2 antisense oligomer with or without other therapeutic agents, and (3) clinically significant treatment regimens for many types of cancers. Thus, Applicants' discovery that a bcl-2 antisense oligomer, when administered for a short treatment cycle, can demonstrate significant therapeutic responses in a patient having a bcl-2 related disorder, provides improved and useful pharmaceutical compositions, treatment courses, and modes of delivery.

The invention is also based, in part, on the discovery that high doses of bcl-2 antisense oligomer, alone and in combination with other therapeutic agents, has reduced toxicity, including unexpectedly few side effects as compared to most standard cancer treatments, and has ameliorative effects in patients suffering from disease. A treatment regimen that encompasses a high dose of bcl-2 antisense oligomer manifests additional benefits to the human subject such as shorter treatment cycles, fewer treatments, or improved efficacy.

In a one embodiment, a bcl-2 antisense oligomer is administered to a human for a short treatment cycle to prevent or treat a bcl-2 related disorder. In another embodiment, a bcl-2 antisense oligomer is administered to a human at high doses to prevent or treat a bcl-2 related disorder. In addition to affecting diseased tissue, the bcl-2 antisense oligomer can protect or treat normal tissues, which include tissues containing cells that normally express the bcl-2 gene. Additionally, the bcl-2 antisense oligomer can protect or treat normal tissues that, although not expressing the bcl-2 gene, are compromised by diseased tissues.

In a specific embodiment, the invention further encompasses the use of combination therapy to prevent or treat a bcl-2 related disorder. Such therapy includes the use of one or more molecules, compounds or treatments that assist in the prevention or treatment of a disease. Examples of contemplated therapeutics include biologicals, chemicals, and therapeutic treatments (e.g., irradiation treatment).

In another specific embodiment, the invention provides for a bcl-2 antisense oligomer that is administered to a human in combination with one of more cancer therapeutic agents to prevent or treat cancer. Such cancer therapeutics include one or more molecules, compounds or treatments that have anticancer activity. Examples of contemplated cancer therapeutics include biologicals, chemicals, and therapeutic treatments (e.g., irradiation treatment).

In yet another specific embodiment, the invention provides for a bcl-2 antisense oligomer that is administered to a human, in combination with one of more cancer therapeutic agents at reduced doses, to prevent or treat cancer. Such treatments may involve high, standard, or low doses of one or more bcl-2 antisense oligomers, treatment cycles may be of long or short duration. In a specific embodiment, the invention provides for a particularly high dose of bcl-2 antisense oligomer that is administered to a human, in combination with one of more cancer therapeutic agents at greatly reduced doses for shortened treatment cycles, to prevent or treat cancer.

5.1 BCL-2 ANTISENSE OLIGOMER

The invention contemplates use of one or more bcl-2 antisense oligomers, or its derivatives, analogues, fragments, hybrids, mimetics, and congeners thereof. As used herein, the term "derivative" refers to any pharmaceutically acceptable homolog, analogue, or fragment corresponding to the pharmaceutical composition of the invention. Antisense oligomers suitable for use in the invention include nucleotide oligomers which range in size from 5 to 10, 10 to 20, 20 to 50, 50 to 75, or 75 to 100 bases in length; preferably 10 to 40 bases in length; more preferably 15 to 25 bases in length; most preferably 18 bases in length. The target sequences may be RNA or DNA, and may be single-stranded or double-stranded. Target molecules include, but are not limited to, pre-mRNA, mRNA, and DNA. In a one embodiment, the target molecule is mRNA. In a preferred embodiment, the target molecule is bcl-2 pre-mRNA or bcl-2 mRNA. In a specific embodiment, the antisense oligomers hybridize to a portion anywhere along the bcl-2 pre-mRNA or mRNA. The antisense oligomers are preferably selected from those oligomers which hybridize to the translation initiation site, donor splicing site, acceptor splicing site, sites for transportation, or sites for degradation of the bcl-2 pre-mRNA or mRNA.

Several bcl-2 antisense oligomers have been assessed previously with variable results (See, e.g., SEQ. ID. NOS.:1-17 in U.S. Pat. No. 5,831,066). Examples of bcl-2 antisense oligomers that may be used in accordance with the present invention are described in detail in U.S. patent application Ser. No. 08/217,082, now U.S. Pat. No. 5,734,033; U.S. patent application Ser. No. 08/465,485, now U.S. Pat. No.

5,831,066; and U.S. patent application Ser. No. 09/080,285, now U.S. Pat. No. 6,040,181, each of which is incorporated herein by reference in its entirety.

In one embodiment, the bcl-2 antisense oligomer is substantially complementary to a portion of a bcl-2 pre-mRNA or mRNA, or to a portion of a pre-mRNA or mRNA that is related to bcl-2. In a preferred embodiment, the bcl-2 antisense oligomer hybridizes to a portion of the translation-initiation site of the pre-mRNA coding strand. In a more preferred embodiment, the bcl-2 antisense oligomer hybridizes to a portion of the pre-mRNA coding strand that comprises the translation-initiation site of the human bcl-2 gene. More preferably, the bcl-2 antisense oligomer comprises a TAC sequence which is complementary to the AUG initiation sequence of the bcl-2 pre-mRNA or RNA.

In another embodiment, the bcl-2 antisense oligomer hybridizes to a portion of the splice donor site of the pre-mRNA coding strand for the human bcl-2 gene. Preferably, this nucleotide comprises a CA sequence, which is complementary to the GT splice donor sequence of the bcl-2 gene, and preferably further comprises flanking portions of 5 to 50 bases, more preferably from about 10 to 20 bases, which hybridizes to portions of the bcl-2 gene coding strand flanking said splice donor site.

In yet another embodiment, the bcl-2 antisense oligomer hybridizes to a portion of the splice acceptor site of the pre-mRNA coding strand for the human bcl-2 gene. Preferably, this nucleotide comprises a TC sequence, which is complementary to the AG splice acceptor sequence of the bcl-2 gene, and preferably further comprises flanking portions of 5 to 50 bases, more preferably from about 10 to 20 bases, which hybridizes to portions of the bcl-2 gene coding strand flanking said splice acceptor site. In another embodiment, the bcl-2 antisense oligomer hybridizes to portions of the pre-mRNA or mRNA involved in splicing, transport or degradation.

One of average skill in the art can recognize that antisense oligomers suitable for use in the invention may also be substantially complementary to other sites along the bcl-2 pre-mRNA or mRNA, and can form hybrids. The skilled artisan will also appreciate that antisense oligomers, which hybridize to a portion of the bcl-2 pre-mRNA or mRNA whose sequence does not commonly occur in transcripts from unrelated genes are preferable so as to maintain treatment specificity.

The design of the sequence of a bcl-2 antisense oligomer can also be determined by empirical testing and assessment of clinical effectiveness, regardless of its degree of sequence homology to, or hybridization with, the bcl-2 gene, bcl-2 pre-mRNA, bcl-2 mRNA, or bcl-2 related nucleotide sequences. One of ordinary skill in the art will appreciate that bcl-2 antisense oligomers having, for example, less sequence homology, greater or fewer modified nucleotides, or longer or shorter lengths, compared to those of the preferred embodiments, but which nevertheless demonstrate responses in clinical treatments, are also within the scope of the invention.

The antisense oligomers may be RNA or DNA, or derivatives thereof. The particular form of antisense oligomer may affect the oligomer's pharmacokinetic parameters such as bioavailability, metabolism, half-life, etc. As such, the invention contemplates antisense oligomer derivatives having properties that improve cellular uptake, enhance nuclease resistance, improve binding to the target sequence, or increase cleavage or degradation of the target sequence. The antisense oligomers may contain bases comprising, for example, phosphorothioates or methylphosphonates. The antisense oligomers, instead, can be mixed oligomers containing combinations of phosphodiesters, phosphorothioate, and/or methylphosphonate nucleotides, among others. Such oligomers may possess modifications which comprise, but are not limited to, 2-O'-alkyl or 2-O'-halo sugar modifications, backbone modifications (e.g., methylphosphonate, phosphorodithioate, phosphordithioate, formacetal, 3'-thioformacetal, sulfone, sulfamate, nitroxide backbone, morpholino derivatives and peptide nucleic acid (PNA) derivatives), or derivatives wherein the base moieties have been modified (Egholm, et al., 1992, *Peptide Nucleic Acids (PNA)-Oligonucleotide Analogues With An Achiral Peptide Backbone*). In another embodiment, antisense oligomers comprise conjugates of the oligonucleotides and derivatives thereof (Goodchild, 1990, "Conjugates of oligonucleotides and modified oligonucleotides: a review of their synthesis and properties", Bioconjug. Chem. 1(3):165-87).

For in vivo therapeutic use, a phosphorothioate derivative of the bcl-2 antisense oligomer is preferable, at least partly because of greater resistance to degradation. In one embodiment, the bcl-2 antisense oligomer is a hybrid oligomer containing phosphorothioate bases. In another embodiment, the bcl-2 antisense oligomer contains at least one phosphorothioate linkage. In another embodiment, the bcl-2 antisense oligomer contains at least three phosphorothioate linkages. In yet another embodiment, the bcl-2 antisense oligomer contains at least three consecutive phosphorothioate linkages. In yet another embodiment, the bcl-2 antisense oligomer is comprised entirely of phosphorothioate linkages. Methods for preparing oligonucleotide derivatives are known in the art. See e.g., Stein et al., 1988, Nucl. Acids Res., 16:3209-21 (phosphorothioate); Blake et al., 1985, Biochemistry 24:6132-38 (methylphosphonate); Morvan et al., 1986, Nucl. Acids Res. 14:5019-32 (alphadeoxynucleotides); Monia et al., 1993, "Evaluation of 2'-modified oligonucleotides containing 2' deoxy gaps as antisense inhibitors of gene expression", J. Biol. Chem. 268:14514-22 (2'-O-methyl-ribonucleosides); Asseline et al., 1984, Proc. Natl. Acad. Sci. USA 81:3297-3301 (acridine); Knorre et al., 1985, Biochemie 67:783-9; Vlassov et al., 1986, Nucl. Acids Res. 14:4065-76 (N-2-chlorocethylamine and phenazine); Webb et al., 1986, Nucl. Acids Res. 14:7661-74 (5-methyl-$N^4$—$N^4$-ethanocytosine); Boutorin et al., 1984, FEBS Letters 172:43-6 (Fe-ethylenediamine tetraacetic acid (EDTA) and analogues); Chi-Hong et al., 1986, Proc. Natl. Acad. Sci. USA 83:7147-51 (5-glycylamido-1,10-o-phenanthroline); and Chu et al., 1985, Proc. Natl. Acad. Sci. USA 82:963-7 (diethylenetriaamine-pentaacetic acid (DTPA) derivatives).

The effective dose of bcl-2 antisense oligomer to be administered during a treatment cycle ranges from about 0.01 to 0.1, 0.1 to 1, or 1 to 10 mg/kg/day. The dose of bcl-2 antisense oligomer to be administered can be dependent on the mode of administration. For example, intravenous administration of a bcl-2 antisense oligomer would likely result in a significantly higher full body dose than a full body dose resulting from a local implant containing a pharmaceutical composition comprising bcl-2 antisense oligomer. In one embodiment, a bcl-2 antisense oligomer is administered subcutaneously at a dose of 0.01 to 10 mg/kg/day; more preferably at a dose of 4 to 9 mg/kg/day; most preferably at a dose of 5 to 7 mg/kg/day. In another embodiment, a bcl-2 antisense oligomer is administered intravenously at a dose of 0.01 to 10 mg/kg/day; more preferably at a dose of 4 to 9 mg/kg/day; most preferably at a dose of 5 to 7 mg/kg/day. In yet another embodiment, a bcl-2 antisense oligomer is administered locally at a dose of 0.01 to 10 mg/kg/day; preferably at a dose of 0.01 to 0.1; more preferably at a dose of 1 to 5 mg/kg/day. It will be evident to one skilled in the art that local administrations can result in lower total body doses. For example, local administration methods such as intratumor administration, intraocular injection, or implantation, can produce locally high concentrations of bcl-2 antisense oligomer, but represent a relatively low dose with respect to total body weight. Thus, in such cases, local administration of a bcl-2 antisense oligomer is contemplated to result in a total body dose of about 0.01 to 5 mg/kg/day.

In another embodiment, a particularly high dose of bcl-2 antisense oligomer, which ranges from about 10 to 20, 20 to 30, or 30 to 50 mg/kg/day, is administered during a treatment cycle.

Moreover, the effective dose of a particular bcl-2 antisense oligomer may depend on additional factors, including the type of cancer, the disease state or stage of disease, the oligomer's toxicity, the oligomer's rate of uptake by cancer cells, as well as the weight, age, and health of the individual to whom the antisense oligomer is to be administered. Because of the many factors present in vivo that may interfere with the action or biological activity of a bcl-2 antisense oligomer, one of ordinary skill in the art can appreciate that an effective amount of a bcl-2 antisense oligomer may vary for each individual.

In another embodiment, a bcl-2 antisense oligomer is at a dose which results in circulating plasma concentrations of the bcl-2 antisense oligomer which is at least 30 nM (nanomolar). As will be apparent to the skilled artisan, lower or higher plasma concentrations of the bcl-2 antisense oligomer may be preferred depending on the mode of administration. For example, plasma concentrations of the bcl-2 antisense oligomer of at least 30 nM can be appropriate in connection with intravenous, subcutaneous, intramuscular, controlled release, and oral administration methods, to name a few. In another example, relatively low circulating plasma levels of the bcl-2 antisense oligomer can be desirable, however, when using local administration methods such as, for example, intratumor administration, intraocular administration, or implantation, which nevertheless can produce locally high, clinically effective concentrations of bcl-2 antisense oligomer.

In yet another embodiment, the circulating plasma concentration of at least 30 nM (nanomolar) of the bcl-2 antisense oligomer is achieved about 1, 2, 3, 4, 5, 6, 7, 8, 9 or 10 hours after the administration of the bcl-2 antisense oligomer. In yet another embodiment, the circulating plasma concentration of at least 30 nM of the bcl-2 antisense oligomer is achieved in about 36 to 48 hours, preferably 24 to 35 hours, more preferably in 12 to 24 hours; most preferably in under 12 hours.

In a specific embodiment, the dose of a bcl-2 antisense oligomer is a high dose. In one embodiment, the circulating plasma concentration of the bcl-2 antisense oligomer is at least 30 nM. In another embodiment, the circulating level of bcl-2 antisense oligomer is 1 µM to 10 µM. In yet another embodiment, the circulating level of bcl-2 antisense oligomer is 1, 2, 3, 4, 5, 6, 7, 8, 9 or 10 µM. In yet another embodiment, the circulating level of bcl-2 antisense oligomer of 1 µM to 10 µM is achieved in about 36 to 48 hours, preferably 24 to 35 hours, more preferably in 12 to 24 hours; most preferably in under 12 hours.

The high dose may be achieved by several administrations per cycle. Alternatively, the high dose may be administered in a single bolus administration. A single administration of a high dose may result in circulating plasma levels of bcl-2 antisense oligomer that are transiently much higher than 30 nM. Moreover, single administrations of particularly high doses of a bcl-2 antisense oligomer may result in a circulating plasma concentration of bcl-2 antisense oligomer of 1 µM to 10 µM in much less 12 hours, even in less than one hour.

Additionally, the dose of a bcl-2 antisense oligomer may vary according to the particular bcl-2 antisense oligomer used. The dose employed is likely to reflect a balancing of considerations, among which are stability, localization, cellular uptake, and toxicity of the particular bcl-2 antisense oligomer. For example, a particular chemically modified bcl-2 antisense oligomer may exhibit greater resistance to degradation, or may exhibit higher affinity for the target nucleic acid, or may exhibit increased uptake by the cell or cell nucleus; all of which may permit the use of low doses. In yet another example, a particular chemically modified bcl-2 antisense oligomer may exhibit lower toxicity than other antisense oligomers, and therefore can be used at high doses. Thus, for a given bcl-2 antisense oligomer, an appropriate dose to administer can be relatively high or relatively low. Appropriate doses would be appreciated by the skilled artisan, and the invention contemplates the continued assessment of optimal treatment schedules for particular species of bcl-2 antisense oligomers. The daily dose can be administered in one or more treatments.

Other factors to be considered in determining an effective dose of a bcl-2 antisense oligomer include whether the oligomer will be administered in combination with other therapeutics. In such cases, the relative toxicity of the other therapeutics may indicate the use of a bcl-2 antisense oligomer at low doses. Alternatively, treatment with a high dose of bcl-2 antisense oligomer can result in combination therapies with reduced doses of therapeutics. In a specific embodiment, treatment with a particularly high dose of bcl-2 antisense oligomer can result in combination therapies with greatly reduced doses of cancer therapeutics. For example, treatment of a patient with 10, 20, 30, 40, or 50 mg/kg/day of a bcl-2 antisense oligomer can further increase the sensitivity of a subject to cancer therapeutics. In such cases, the particularly high dose of bcl-2 antisense oligomer is combined with, for example, a greatly shortened radiation therapy schedule. In another example, the particularly high dose of a bcl-2 antisense oligomer produces significant enhancement of the potency of cancer therapeutic agents.

Additionally, the particularly high doses of bcl-2 antisense oligomer may further shorten the period of administration of a therapeutically effective amount of bcl-2 antisense oligomer and/or cancer therapeutic, such that the length of a treatment cycle is much shorter than 14 days.

In one embodiment, an 18-base phosphorothioate bcl-2 antisense oligomer of the sequence 5'-TCTCCCAGCGT-GCGCCAT-3' (SEQ ID NO:17), which is complimentary to the first six codons of the bcl-2 mRNA and hybridizes to the respective target RNA bases, is administered for a short treatment cycle, defined as less than two weeks.

In one embodiment, G3139 is administered for 2 to 13 days at a dose of 0.01 to 10 mg/kg/day. In a specific embodiment, G3139 is administered for 2 to 3, 4 to 5, 6 to 7, 8 to 9, 10 to 11, or 12 to 13 days at a dose of 0.01 to 1, 1 to 2, 3 to 4, 5 to 6, 6 to 7, 7 to 8, or 9 to 10 mg/kg/day; more preferably at a dose of 4 to 9 mg/kg/day, and most preferably at a dose of 5 to 7 mg/kg/day. In another embodiment, G3139 is administered at said dose for 3 to 9 days. In yet another embodiment, G3139 is administered at said dose for 4 to 7 days. In a preferred embodiment, G3139 is administered at said dose for 5 to 6 days. In a most preferred embodiment, G3139 is administered at a dose of 5 to 7 mg/kg/day for 5 to 6 days. The invention contemplates other preferred treatment regimens depending on the particular bcl-2 antisense oligomer to be used, or depending on the particular mode of administration, or depending on whether the bcl-2 antisense oligomer is administered as part of a combination therapy, e.g., in combination with a cancer therapeutic agent. The daily dose can be administered in one or more treatments.

In another embodiment, G3139 is administered at a particularly high dose of about 10 to 50 mg/kg/day. In a specific embodiment, G3139 is administered at a particularly high dose of about 10 to 15, 16 to 20, 21 to 25, 26 to 30, 31 to 35, 36 to 40, 41 to 45, or 46 to 50 mg/kg/day. In a further embodiment, G3139 is administered at said dose for 1 to 10 days. In yet another embodiment, G3139 is administered at said dose for 2 to 7 days. In a yet another embodiment, G3139 is administered at said dose for 3 to 4 days. In a preferred embodiment, G3139 is administered at a dose of 26 to 30, 31 to 35, 36 to 40, 41 to 45, or 46 to 50 mg/kg/day for a minimum of 1 day. The invention contemplates other preferred treatment regimens depending on the particular bcl-2 antisense oligomer to be used, or depending on the particular mode of administration, or depending on whether the bcl-2 antisense oligomer is administered as part of a combination therapy, e.g., in combination with a cancer therapeutic agent. The daily dose can be administered in one or more treatments.

5.2 CANCER THERAPEUTICS

The invention described herein encompasses a method of preventing or treating cancer comprising a therapeutically effective amount of a bcl-2 antisense oligomer, including but not limited to high doses of the oligomer, to a human in need of such therapy. The invention further encompasses the use of a short period of administration of a bcl-2 antisense oligomer. Normal, non-cancerous cells divide at a frequency characteristic for the particular cell type. When a cell has been transformed into a cancerous state, uncontrolled cell proliferation and reduced cell death results, and therefore, promiscuous cell division or cell growth is a hallmark of a cancerous cell type. Examples of types of cancer, include, but are not limited to, non-Hodgkin's lymphoma, Hodgkin's lymphoma, leukemia (e.g., acute leukemia such as acute lymphocytic leukemia, acute myelocytic leukemia, chronic myeloid leukemia, chronic lymphocytic leukemia, multiple myeloma), colon carcinoma, rectal carcinoma, pancreatic cancer, breast cancer, ovarian cancer, prostate cancer, renal cell carcinoma, hepatoma, bile duct carcinoma, choriocarcinoma, cervical cancer, testicular cancer, lung carcinoma, bladder carcinoma, melanoma, head and neck cancer, brain cancer, cancers of unknown primary site, neoplasms, cancers of the peripheral nervous system, cancers of the central nervous system, tumors (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, seminoma, embryonal carcinoma, Wilms' tumor, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, and retinoblastoma), heavy chain disease, metastases, or any disease or disorder characterized by uncontrolled or abnormal cell growth.

In a preferred embodiment, the invention further encompasses the use of combination therapy to prevent or treat cancer. For example, prostate cancer can be treated with a pharmaceutical composition comprising a bcl-2 antisense oligomer in combination with paclitaxel, docetaxel, mitoxantrone, and/or an androgen receptor antagonist (e.g., flutamide). As another example, breast cancer can be treated with a pharmaceutical composition comprising a bcl-2 antisense oligomer in combination with docetaxel, paclitaxel, cisplatin, 5-fluorouracil, doxorubicin, and/or VP-16 (etoposide). As another example, leukemia can be treated with a pharmaceutical composition comprising a bcl-2 antisense oligomer in combination with fludarabine, cytosine arabinoside, gemtuzumab (MYLOTARG), daunorubicin, methotrexate, vincristine, 6-mercaptopurine, idarubicin, mitoxantrone, etoposide, asparaginase, prednisone and/or cyclophosphamide. As another example, myeloma can be treated with a pharmaceutical composition comprising a bcl-2 antisense oligomer in combination with dexamethasone. As another example, melanoma can be treated with a pharmaceutical composition comprising a bcl-2 antisense oligomer in combination with dacarbazine. As another example, colorectal cancer can be treated with a pharmaceutical composition comprising a bcl-2 antisense oligomer in combination with irinotecan. As another example, lung cancer can be treated with a pharmaceutical composition comprising a bcl-2 antisense oligomer in combination with paclitaxel, docetaxel, etoposide and/or cisplatin. As another example, non-Hodgkin's lymphoma can be treated with a pharmaceutical composition comprising a bcl-2 antisense oligomer in combination with cyclophosphamide, CHOP, etoposide, bleomycin, mitoxantrone and/or cisplatin. As another example, gastric cancer can be treated with a pharmaceutical composition comprising a bcl-2 antisense oligomer in combination with cisplatin. As another example, pancreatic cancer can be treated with a pharmaceutical composition comprising a bcl-2 antisense oligomer in combination with gemcitabine. These combination therapies can also be used to prevent cancer or the recurrence of cancer. Combination therapy also includes, in addition to administration of a bcl-2 antisense oligomer, the use of one or more molecules, compounds or treatments that aid in the prevention or treatment of cancer, which molecules, compounds or treatments includes, but is not limited to, chemoagents, immunotherapeutics, cancer vaccines, anti-angiogenic agents, cytokines, hormone therapies, gene therapies, and radiotherapies.

In one embodiment, one or more chemoagents, in addition to a bcl-2 antisense oligomer, is administered to treat a cancer patient. Examples of chemoagents contemplated by the present invention include, but are not limited to, cytosine arabinoside, taxoids (e.g., paclitaxel, docetaxel), anti-tubulin agents (e.g., paclitaxel, docetaxel, Epothilone B, or its analogues), cisplatin, carboplatin, adriamycin, tenoposide, mitozantron, 2-chlorodeoxyadenosine, alkylating agents (e.g., cyclophosphamide, mechlorethamine, thioepa, chlorambucil, melphalan, carmustine (BSNU), lomustine (CCNU), cyclothosphamide, busulfan, dibromomannitol, streptozotocin, mitomycin C, and cis-dichlorodiamine platinum (II) (DDP) cisplatin, thio-tepa), antibiotics (e.g., dactinomycin (formerly actinomycin), bleomycin, mithramycin, anthramycin), antimetabolites (e.g., methotrexate, 6-mercaptopurine, 6-thioguanine, cytarabine, 5-fluorouracil, fludarabine, gemcitabine, dacarbazine, temozolamide), asparaginase, Bacillus Calmette and Guerin, diphtheria toxin, hexamethylmelamine, hydroxyurea, LYSODREN®, nucleoside analogues, plant alkaloids (e.g., Taxol, paclitaxel, camptothecin, topotecan, irinotecan (CAMPTOSAR, CPT-11), vincristine, vinca alkyloids such as vinblastine), podophyllotoxin (including derivatives such as epipodophyllotoxin, VP-16 (etoposide), VM-26 (teniposide)), cytochalasin B, gramicidin D, ethidium bromide, emetine, mitomycin, procarbazine, mechlorethamine, anthracyclines (e.g., daunorubicin (formerly daunomycin), doxorubicin, doxorubicin liposomal), dihydroxyanthracindione, mitoxantrone, mithramycin, actinomycin D, procaine, tetracaine, lidocaine, propranolol, puromycin, anti-mitotic agents, abrin, ricin A, pseudomonas exotoxin, nerve growth factor, platelet derived growth factor, tissue plasminogen activator, aldesleukin, allutamine, anastrozle, bicalutamide, biaomycin, busulfan, capecitabine, carboplain, chlorabusil, cladribine, cylarabine, daclinomycin, estramusine, floxuridhe, gamcitabine, gosereine, idarubicin, itosfamide, lauprolide acetate, levamisole, lomusline, mechlorethamine, magestrol, acetate, mercaptopurino, mesna, mitolanc, pegaspergase, pentoslatin, picamycin, riuxlmab, campath-1, straplozocin, thioguanine, tretinoin, vinorelbine, or any fragments, family members, or derivatives thereof, including pharmaceutically acceptable salts thereof. Compositions comprising one or more chemoagents (e.g., FLAG, CHOP) are also contemplated by the present invention. FLAG comprises fludarabine, cytosine arabinoside (Ara-C) and G-CSF. CHOP comprises cyclophosphamide, vincristine, doxorubicin, and prednisone.

In one embodiment, said chemoagent is dacarbazine at a dose ranging from 200 to 4000 mg/m$^2$/cycle. In a preferred embodiment, said dose ranges from 700 to 1000 mg/m$^2$/cycle. In another embodiment, said chemoagent is fludarabine at a dose ranging from 25 to 50 mg/m$^2$/cycle. In another embodiment, said chemoagent is cytosine arabinoside (Ara-C) at a dose ranging from 200 to 2000 mg/m$^2$/cycle. In another embodiment, said chemoagent is docetaxel at a dose ranging from 1.5 to 7.5 mg/kg/cycle. In another embodiment, said chemoagent is paclitaxel at a dose ranging from 5 to 15 mg/kg/cycle. In yet another embodiment, said chemoagent is cisplatin at a dose ranging from 5 to 20 mg/kg/cycle. In yet another embodiment, said chemoagent is 5-fluorouracil at a dose ranging from 5 to 20 mg/kg/cycle. In yet another embodiment, said chemoagent is doxorubicin at a dose ranging from 2 to 8 mg/kg/cycle. In yet another embodiment, said chemoagent is epipodophyllotoxin at a dose ranging from 40 to 160 mg/kg/cycle. In yet another embodiment, said chemoagent is cyclophosphamide at a dose ranging from 50 to 200 mg/kg/cycle. In yet another embodiment, said chemoagent is irinotecan at a dose ranging from 50 to 75, 75 to 100, 100 to 125, or 125 to 150 mg/m$^2$/cycle. In yet another embodiment, said chemoagent is vinblastine at a dose ranging from 3.7 to 5.4, 5.5 to 7.4, 7.5 to 11, or 11 to 18.5 mg/m$^2$/cycle. In yet another embodiment, said chemoagent is vincristine at a dose ranging from 0.7 to 1.4, or 1.5 to 2 mg/m$^2$/cycle. In yet another embodiment, said chemoagent is methotrexate at a dose ranging from 3.3 to 5, 5 to 10, 10 to 100, or 100 to 1000 mg/m$^2$/cycle.

In a preferred embodiment, the invention further encompasses the use of low doses of chemoagents when administered as part of a bcl-2 antisense oligomer treatment regimen.

For example, initial treatment with a bcl-2 antisense oligomer increases the sensitivity of a tumor to subsequent challenge with a dose of chemoagent, which dose is near or below the lower range of dosages when the chemoagent is administered without a bcl-2 antisense oligomer. In one embodiment, a bcl-2 antisense oligomer and a low dose (e.g., 6 to 60 mg/m$^2$ day or less) of docetaxel are administered to a cancer patient. In another embodiment, a bcl-2 antisense oligomer and a low dose (e.g., 10 to 135 mg/m$^2$/day or less) of paclitaxel are administered to a cancer patient. In yet another embodiment, a bcl-2 antisense oligomer and a low dose (e.g., 2.5 to 25 mg/m$^2$/day or less) of fludarabine are administered to a cancer patient. In yet another embodiment, a bcl-2 antisense oligomer and a low dose (e.g., 0.5 to 1.5 g/m$^2$/day or less) of cytosine arabinoside (Ara-C) are administered to a cancer patient.

The invention, therefore, contemplates the use of one or more bcl-2 antisense oligomers, which is administered prior to, subsequently, or concurrently with low doses of chemoagents, for the prevention or treatment of cancer.

In one embodiment, said chemoagent is cisplatin, e.g., PLATINOL or PLATINOL-AQ (Bristol Myers), at a dose ranging from 5 to 10, 10 to 20, 20 to 40, or 40 to 75 mg/m$^2$/cycle. In another embodiment, a dose of cisplatin ranging from 7.5 to 75 mg/m$^2$/cycle is administered to a patient with ovarian cancer. In another embodiment, a dose of cisplatin ranging from 5 to 50 mg/m$^2$/cycle is administered to a patient with bladder cancer.

In another embodiment, said chemoagent is carboplatin, e.g., PARAPLATIN (Bristol Myers), at a dose ranging from 2 to 4, 4 to 8, 8 to 16, 16 to 35, or 35 to 75 mg/m$^2$/cycle. In another embodiment, a dose of carboplatin ranging from 7.5 to 75 mg/m$^2$/cycle is administered to a patient with ovarian cancer. In another embodiment, a dose of carboplatin ranging from 5 to 50 mg/m$^2$/cycle is administered to a patient with bladder cancer. In another embodiment, a dose of carboplatin ranging from 2 to 20 mg/m$^2$/cycle is administered to a patient with testicular cancer.

In another embodiment, said chemoagent is cyclophosphamide, e.g., CYTOXAN (Bristol Myers Squibb), at a dose ranging from 0.25 to 0.5, 0.5 to 1, 1 to 2, 2 to 5, 5 to 10, 10 to 20, 20 to 40 mg/kg/cycle. In another embodiment, a dose of cyclophosphamide ranging from 4 to 40 mg/kg/cycle is administered to a patient with malignant cancer. In another embodiment, a dose of cyclophosphamide ranging from 0.25 to 2.5 mg/kg/cycle is administered to a patient with non-malignant cancer.

In one embodiment, said chemoagent is cytarabine, e.g., CYTOSAR-U (Pharmacia & Upjohn), at a dose ranging from 0.5 to 1, 1 to 4, 4 to 10, 10 to 25, 25 to 50, or 50 to 100 mg/m$^2$/cycle. In another embodiment, a dose of cytarabine ranging from 10 to 100 mg/m$^2$/cycle is administered to a patient with acute leukemia. In another embodiment, a dose of cytarabine ranging from 0.5 to 5 mg/m$^2$/cycle is administered to a patient with meningeal leukemia. In another embodiment, a dose of cytarabine liposome, e.g., DEPOCYT (Chiron Corp.) ranging from 5 to 50 mg/m$^2$/cycle is administered to a patient with cancer.

In another embodiment, said chemoagent is dacarbazine, e.g., DTIC or DTIC-DOME (Bayer Corp.), at a dose ranging from 15 to 250 mg/m$^2$/cycle or ranging from 0.2 to 2 mg/kg/cycle. In another embodiment, a dose of dacarbazine ranging from 15 to 150 mg/m$^2$/cycle is administered to a patient with Hodgkin's disease. In another embodiment, a dose of dacarbazine ranging from 0.2 to 2 mg/kg/cycle is administered to a patient with malignant melanoma.

In another embodiment, said chemoagent is topotecan, e.g., HYCAMTIN (SmithKline Beecham), at a dose ranging from 0.1 to 0.2, 0.2 to 0.4, 0.4 to 0.8, or 0.8 to 1.5 mg/m$^2$/cycle.

In another embodiment, said chemoagent is irinotecan, e.g., CAMPTOSAR (Pharmacia & Upjohn), at a dose ranging from 5 to 10, 10 to 25, or 25 to 50 mg/m$^2$/cycle.

In another embodiment, said chemoagent is fludarabine, e.g., FLUDARA (Berlex Laboratories), at a dose ranging from 2.5 to 5, 5 to 10, 10 to 15, or 15 to 25 mg/m$^2$/cycle.

In another embodiment, said chemoagent is cytosine arabinoside (Ara-C) at a dose ranging from 200 to 2000 mg/m$^2$/cycle.

In another embodiment, said chemoagent is docetaxel, e.g., TAXOTERE (Rhone Poulenc Rorer) at a dose ranging from 6 to 10, 10 to 30, or 30 to 60 mg/m$^2$/cycle.

In another embodiment, said chemoagent is paclitaxel, e.g., TAXOL (Bristol Myers Squibb), at a dose ranging from 10 to 20, 20 to 40, 40 to 70, or 70 to 135 mg/kg/cycle.

In another embodiment, said chemoagent is 5-fluorouracil at a dose ranging from 0.5 to 5 mg/kg/cycle.

In another embodiment, said chemoagent is doxorubicin, e.g., ADRIAMYCIN (Pharmacia & Upjohn), DOXIL (Alza), RUBEX (Bristol Myers Squibb), at a dose ranging from 2 to 4, 4 to 8, 8 to 15, 15 to 30, or 30 to 60 mg/kg/cycle.

In another embodiment, said chemoagent is etoposide, e.g., VEPESID (Pharmacia & Upjohn), at a dose ranging from 3.5 to 7, 7 to 15, 15 to 25, or 25 to 50 mg/m$^2$/cycle. In another embodiment, a dose of etoposide ranging from 5 to 50 mg/m$^2$/cycle is administered to a patient with testicular cancer. In another embodiment, a dose of etoposide ranging from 3.5 to 35 mg/m$^2$/cycle is administered to a patient with small cell lung cancer.

In another embodiment, said chemoagent is vinblastine, e.g., VELBAN (Eli Lilly), at a dose ranging from 0.3 to 0.5, 0.5 to 1, 1 to 2, 2 to 3, or 3 to 3.7 mg/m$^2$/cycle.

In another embodiment, said chemoagent is vincristine, e.g., ONCOVIN (Eli Lilly), at a dose ranging from 0.1, 0.2, 0.3, 0.4, 0.5, 0.6 or 0.7 mg/m$^2$/cycle.

In another embodiment, said chemoagent is methotrexate at a dose ranging from 0.2 to 0.9, 1 to 5, 5 to 10, 10 to 20.

In another embodiment, a bcl-2 antisense oligomer is administered in combination with one or more immunotherapeutic agents, such as antibodies and immunomodulators, which includes, but is not limited to, rituxan, rituximab, campath-1, gemtuzumab, or trastuzumab.

In another embodiment, a bcl-2 antisense oligomer is administered in combination with one or more antiangiogenic agents, which includes, but is not limited to, angiostatin, thalidomide, kringle 5, endostatin, Serpin (Serine Protease Inhibitor) anti-thrombin, 29 kDa N-terminal and a 40 kDa C-terminal proteolytic fragments of fibronectin, 16 kDa proteolytic fragment of prolactin, 7.8 kDa proteolytic fragment of platelet factor-4, a 13-amino acid peptide corresponding to a fragment of platelet factor-4 (Maione et al., 1990, Cancer Res. 51:2077-2083), a 14-amino acid peptide corresponding to a fragment of collagen I (Tolma et al., 1993, J. Cell Biol. 122:497-511), a 19 amino acid peptide corresponding to a fragment of Thrombospondin I (Tolsma et al., 1993, J. Cell Biol. 122:497-511), a 20-amino acid peptide corresponding to a fragment of SPARC (Sage et al., 1995, J. Cell. Biochem. 57:1329-1334), or any fragments, family members, or derivatives thereof, including pharmaceutically acceptable salts thereof.

Other peptides that inhibit angiogenesis and correspond to fragments of laminin, fibronectin, procollagen, and EGF have also been described (see the review by Cao, 1998, Prog. Mol. Subcell. Biol. 20:161-176). Monoclonal antibodies and cyclic pentapeptides, which block certain integrins that bind RGD proteins (i.e., possess the peptide motif Arg-Gly-Asp), have been demonstrated to have anti-vascularization activities (Brooks et al., 1994, Science 264:569-571; Hammes et al., 1996, Nature Medicine 2:529-533). Moreover, inhibition of the urokinase plasminogen activator receptor by receptor antagonists inhibits angiogenesis, tumor growth and metastasis (Min et al., 1996, Cancer Res. 56: 2428-33; Crowley et al., 1993, Proc. Natl. Acad. Sci. USA 90:5021-25). Use of such antiangiogenic agents is also contemplated by the present invention.

In another embodiment, a bcl-2 antisense oligomer is administered in combination with a regimen of radiation.

In another embodiment, a bcl-2 antisense oligomer is administered in combination with one or more cytokines, which includes, but is not limited to, lymphokines, tumor necrosis factors, tumor necrosis factor-like cytokines, lymphotoxin-α, lymphotoxin-β, interferon-α, interferon-β, macrophage inflammatory proteins, granulocyte monocyte colony stimulating factor, interleukins (including, but not limited to, interleukin-1, interleukin-2, interleukin-6, interleukin-12, interleukin-15, interleukin-18), OX40, CD27, CD30, CD40 or CD137 ligands, Fas-Fas ligand, 4-1BBL, endothelial monocyte activating protein or any fragments, family members, or derivatives thereof, including pharmaceutically acceptable salts thereof.

In yet another embodiment, a bcl-2 antisense oligomer is administered in combination with a cancer vaccine. Examples of cancer vaccines include, but are not limited to, autologous cells or tissues, non-autologous cells or tissues, carcinoembryonic antigen, alpha-fetoprotein, human chorionic gonadotropin, BCG live vaccine, melanocyte lineage proteins (e.g., gp100, MART-1/MelanA, TRP-1 (gp75), tyrosinase, widely shared tumor-specific antigens (e.g., BAGE, GAGE-1, GAGE-2, MAGE-1, MAGE-3, N-acetylglucosaminyltransferase-V, p15), mutated antigens that are tumor-specific (β-catenin, MUM-1, CDK4), nonmelanoma antigens (e.g., HER-2/neu (breast and ovarian carcinoma), human papillomavirus-E6, E7 (cervical carcinoma), MUC-1 (breast, ovarian and pancreatic carcinoma)). For human tumor antigens recognized by T cells, see generally Robbins and Kawakami, 1996, Curr. Opin. Immunol. 8:628-36. Cancer vaccines may or may not be purified preparations.

In yet another embodiment, a bcl-2 antisense oligomer is used in association with a hormonal treatment. Hormonal therapeutic treatments comprise hormonal agonists, hormonal antagonists (e.g., flutamide, tamoxifen, leuprolide acetate (LUPRON)), and steroids (e.g., dexamethasone, retinoids, betamethasone, cortisol, cortisone, prednisone, dehydrotestosterone, glucocorticoids, mineralocorticoids, estrogen, testosterone, progestins).

In yet another embodiment, a bcl-2 antisense oligomer is used in association with a gene therapy program in the treatment of cancer.

In one embodiment, a bcl-2 antisense oligomer is administered, in combination with at least one cancer therapeutic agent, for a short treatment cycle to a cancer patient to treat cancer. In one embodiment, said treatment cycle ranges from 2 to 13 days. In another embodiment, said treatment cycle ranges from 3 to 9 days. In another embodiment, said treatment cycle ranges from 4 to 7 days. In yet another embodiment, said treatment cycle ranges from 5 to 6 days. The duration of treatment with the cancer therapeutic agent may vary according to the particular cancer therapeutic agent used. The invention also contemplates discontinuous administration or daily doses divided into several partial administrations. An appropriate treatment time for a particular cancer therapeutic agent will be appreciated by the skilled artisan, and the invention contemplates the continued assessment of optimal treatment schedules for each cancer therapeutic agent.

The present invention contemplates at least one cycle, preferably more than one cycle during which a single therapeutic or sequence of therapeutics is administered. In a preferred embodiment, the cycle is shorter than 14 days. In one embodiment, the length of one cycle is 10-13 days. In a preferred embodiment, the length of one cycle is 7-9 days. In a most preferred embodiment, the length of one cycle is 5-6 days. An appropriate period of time for one cycle will be appreciated by the skilled artisan, as will the total number of cycles, and the interval between cycles. The invention contemplates the continued assessment of optimal treatment schedules for each bcl-2 antisense oligomer and cancer therapeutic agent.

5.3 PHARMACEUTICAL COMPOSITIONS

The present invention further provides for a pharmaceutical composition that comprises a bcl-2 antisense oligomer and a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, saline solutions, glycerol solutions, ethanol, N-(1(2,3-dioleyloxy)propyl)-N,N,N-trimethylammonium chloride (DOTMA), diolesylphosphotidylethanolamine (DOPE), and liposomes. Such compositions should contain a therapeutically effective amount of the compound, together with a suitable amount of carrier so as to provide the form for proper administration to the patient. The formulation should suit the mode of administration. For example, oral administration requires enteric coatings to protect the antisense oligomer from degradation within the gastrointestinal tract. In another example, the antisense oligomer may be administered in a liposomal formulation to shield the antisense oligomer from degradative enzymes, facilitate transport in circulatory system, and effect delivery across cell membranes to intracellular sites.

In another embodiment, a pharmaceutical composition comprises a bcl-2 antisense oligomer and one or more therapeutic agents and a pharmaceutically acceptable carrier. In a particular embodiment, the pharmaceutical composition comprises a bcl-2 antisense oligomer and one or more cancer therapeutic agents and a pharmaceutically acceptable carrier.

In one embodiment, a pharmaceutical composition, comprising a bcl-2 antisense oligomer, with or without other therapeutic agents, and a pharmaceutically acceptable carrier, is at an effective dose.

In one embodiment, the pharmaceutical composition comprises a bcl-2 antisense oligomer at a dose of about 0.01 to 0.1, 0.1 to 1, 1 to 5, or 6 to 10 mg/kg/day; preferably at a dose of 4 to 9 mg/kg/day; more preferably at a dose of 5 to 7 mg/kg/day; and a pharmaceutically acceptable carrier. The actual amount of any particular antisense oligomer administered can depend on several factors, such as the type of cancer, the toxicity of the antisense oligomer to normal cells of the body, the rate of uptake of the antisense oligomer by tumor cells, and the weight and age of the individual to whom the antisense oligomer is administered. Because of the many factors present in vivo that may interfere with the action or biological activity of the antisense oligomer, an effective amount of the antisense oligomer may vary for each individual.

In another embodiment, the pharmaceutical compositions of the invention comprise a bcl-2 antisense oligomer at a particularly high dose, which ranges from about 10 to 50 mg/kg/day. In a specific embodiment a particularly high dose of bcl-2 antisense oligomer, ranging from 11 to 15, 16 to 20, 21 to 25, 26 to 30, 31 to 35, 36 to 40, 41 to 45, or 46 to 50 mg/kg/day mg/kg/day, is administered during a treatment cycle.

Selection of the preferred effective dose can be determined (e.g., via clinical trials) by a skilled artisan based upon the consideration of several factors which will be known to one of ordinary skill in the art. Such factors include the particular form of antisense oligomer, the oligomer's pharmacokinetic parameters such as bioavailability, metabolism, half-life, etc., which is established during the development procedures typically employed in obtaining regulatory approval of a pharmaceutical compound. Further factors in considering the dose include the disease to be treated, the benefit to be achieved in a patient, the patient's body mass, the patient's immune status, the route of administration, whether administration of the antisense oligomer or combination therapeutic agent is acute or chronic, concomitant medications, and other factors known by the skilled artisan to affect the efficacy of administered pharmaceutical agents.

The compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In a preferred embodiment, the composition is formulated in accordance with routine procedures as a pharmaceutical composition adapted for subcutaneous injection or intravenous administration to humans. Typically, compositions for subcutaneous injection or intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where the composition is to be administered by infusion, it can be dispensed with an infusion bottle, bag, or other acceptable container, containing sterile pharmaceutical grade water, saline, or other acceptable diluents. Where the composition is administered by injection, an ampule of sterile water for injection or saline can be provided so that the ingredients may be mixed prior to administration.

5.4 MODES OF ADMINISTRATION

Administration of the pharmaceutical compositions of the invention includes, but is not limited to, oral, intravenous infusion, subcutaneous injection, intramuscular, topical, depo injection, implantation, time-release mode, intracavitary, intranasal, inhalation, intratumor, intraocular, and controlled release. The pharmaceutical compositions of the invention also may be introduced parenterally, transmucosally (e.g., orally), nasally, rectally, intravaginally, sublingually, submucosally, or transdermally. Preferably, administration is parenteral, i.e., not through the alimentary canal but rather through some other route via, for example, intravenous, subcutaneous, intramuscular, intraperitoneal, intraorbital, intracapsular, intraspinal, intrasternal, intra-arterial, or intradermal administration. The skilled artisan can appreciate the specific advantages and disadvantages to be considered in choosing a mode of administration. Multiple modes of administration are encompassed by the invention. For example, a bcl-2 antisense oligomer is administered by subcutaneous injection, whereas a combination therapeutic agent is administered by intravenous infusion. Moreover, administration of one or more species of bcl-2 antisense oligomer, with or without other therapeutic agents, may occur simultaneously (i.e., co-administration) or sequentially. For example, a bcl-2 antisense oligomer is first administered to increase sensitivity of a tumor to subsequent administration of a cancer therapeutic agent or irradiation therapy. In another embodiment, the periods of administration of one or more species of bcl-2 antisense oligomer, with or without other therapeutic agents may overlap. For example, a bcl-2 antisense oligomer is administered for 7 days, and a second therapeutic agent is introduced beginning on the fifth day of bcl-2 antisense oligomer treatment, and treatment with the second therapeutic agent continues beyond the 7-day bcl-2 antisense oligomer treatment.

Pharmaceutical compositions adapted for oral administration may be provided, for example, as capsules or tablets; as powders or granules; as solutions, syrups or suspensions (in aqueous or non-aqueous liquids); as edible foams or whips; or as emulsions. Tablets or hard gelatine capsules may comprise, for example, lactose, starch or derivatives thereof, magnesium stearate, sodium saccharine, cellulose, magnesium carbonate, stearic acid or salts thereof. Soft gelatine capsules may comprise, for example, vegetable oils, waxes, fats, semi-solid, or liquid polyols etc. Solutions and syrups may comprise, for example, water, polyols and sugars.

An active agent intended for oral administration may be coated with or admixed with a material (e.g., glyceryl monostearate or glyceryl distearate) that delays disintegration or affects absorption of the active agent in the gastrointestinal tract. Thus, for example, the sustained release of an active agent may be achieved over many hours and, if necessary, the active agent can be protected from being degraded within the gastrointestinal tract. Taking advantage of the various pH and enzymatic conditions along the gastrointestinal tract, pharmaceutical compositions for oral administration may be formulated to facilitate release of an active agent at a particular gastrointestinal location.

Pharmaceutical compositions adapted for parenteral administration include, but are not limited to, aqueous and non-aqueous sterile injectable solutions or suspensions, which may contain antioxidants, buffers, bacteriostats and solutes that render the compositions substantially isotonic with the blood of an intended recipient. Other components that may be present in such compositions include water, alcohols, polyols, glycerine and vegetable oils, for example. Compositions adapted for parenteral administration may be presented in unit-dose or multi-dose containers, for example sealed ampules and vials, and may be stored in a freeze-dried (lyophilized) condition requiring the addition of a sterile liquid carrier, e.g., sterile saline solution for injections, immediately prior to use. Extemporaneous injection solutions and suspensions may be prepared from sterile powders, granules and tablets. Such compositions should contain a therapeutically effective amount of a bcl-2 antisense oligomer or other therapeutic agent, together with a suitable amount of carrier so as to provide the form for proper administration to the patient. The formulation should suit the mode of administration.

Pharmaceutical compositions adapted for transdermal administration may be provided as discrete patches intended to remain in intimate contact with the epidermis for a prolonged period of time. Pharmaceutical compositions adapted for topical administration may be provided as, for example, ointments, creams, suspensions, lotions, powders, solutions, pastes, gels, sprays, aerosols or oils. A topical ointment or cream is preferably used for topical administration to the skin, mouth, eye or other external tissues. When formulated in an ointment, the active ingredient may be employed with either a paraffinic or a water-miscible ointment base. Alternatively, the active ingredient may be formulated in a cream with an oil-in-water base or a water-in-oil base.

Pharmaceutical compositions adapted for topical administration to the eye include, for example, eye drops or injectable compositions. In these compositions, the active ingredient can be dissolved or suspended in a suitable carrier, which includes, for example, an aqueous solvent with or without carboxymethylcellulose. Pharmaceutical compositions adapted for topical administration in the mouth include, for example, lozenges, pastilles and mouthwashes.

Pharmaceutical compositions adapted for nasal administration may comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, compositions adopted for nasal administration may comprise liquid carriers such as, for example, nasal sprays or nasal drops. These compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient.

Pharmaceutical compositions adapted for rectal administration may be provided as suppositories or enemas. Pharmaceutical compositions adapted for vaginal administration may be provided, for example, as pessaries, tampons, creams, gels, pastes, foams or spray formulations.

In one embodiment, a pharmaceutical composition of the invention is delivered by a controlled-release system. For example, the pharmaceutical composition may be administered using intravenous infusion, an implantable osmotic pump, a transdermal patch, liposomes, or other modes of administration. In one embodiment, a pump may be used (See e.g., Langer, 1990, Science 249:1527-33; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, the compound can be delivered in a vesicle, in particular a liposome (See e.g., Langer, Science 249:1527-33 (1990); Treat et al., 1989, in *Liposomes in the Therapy of Infectious Disease and Cancer*, Lopez-Berestein and Fidler (eds.), Liss, New York, pp. 353-65; Lopez-Berestein, ibid., pp. 317-27 International Patent Publication No. WO 91/04014; U.S. Pat. No. 4,704,355). In another embodiment, polymeric materials can be used (See e.g., *Medical Applications of Controlled Release*, Langer and Wise (eds.), CRC Press: Boca Raton, Fla., 1974; *Controlled Drug Bioavailability, Drug Product Design and Performance*, Smolen and Ball (eds.), Wiley: New York (1984); Ranger and Peppas, 1953, J. Macromol. Sci. Rev. Macromol. Chem. 23:61; Levy et al., 1985, Science 228:190; During et al., 1989, Ann. Neurol. 25:351; Howard et al., 1989, J. Neurosurg. 71:105).

In yet another embodiment, a controlled release system can be placed in proximity of the target. For example, a micropump may deliver controlled doses directly into the brain, thereby requiring only a fraction of the systemic dose (See e.g., Goodson, 1984, in *Medical Applications of Controlled Release*, vol. 2, pp. 115-138).

In one embodiment, it may be desirable to administer the pharmaceutical composition of the invention locally to the area in need of treatment; this may be achieved, for example, and not by way of limitation, by local infusion during surgery, topical application (e.g., in conjunction with a wound dressing after surgery), injection, by means of a catheter, by means of a suppository, or by means of an implant. An implant can be of a porous, non-porous, or gelatinous material, including membranes, such as sialastic membranes, or fibers.

Suppositories generally contain active ingredients in the range of 0.5% to 10% by weight. Oral formulations preferably contain 10% to 95% active ingredient by weight.

A bcl-2 antisense oligomer can be administered before, during, and/or after the administration of one or more therapeutic agents. In one embodiment, a bcl-2 antisense oligomer can first be administered to reduce the expression of bcl-2, which increases the tumor's sensitivity to subsequent challenge with a cancer therapeutic agent. In another embodiment, a bcl-2 antisense oligomer can be administered after administration of a cancer therapeutic agent to reduce tumor expression of bcl-2, which can deter tumor resistance, and thereby prevent relapse or minimization of response to the cancer therapeutic agent. In yet another embodiment, there can be a period of overlap between the administration of bcl-2 antisense oligomer and one or more therapeutic agents.

The invention further provides a pharmaceutical kit comprising an effective amount of a bcl-2 oligomer, in combination with a cancer therapeutic agent, to protect from or treat a bcl-2 related disorder. In one embodiment, the effective amount of a bcl-2 oligomer and a pharmaceutically acceptable carrier may be packaged in a single dose vial or other container. In a specific embodiment, the bcl-2 oligomer comprises G3139 (SEQ. ID. NO.:17). The kit may comprise one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention may be better understood by reference to the following non-limiting Examples, which are provided only as exemplary of the invention. The following examples are presented to more fully illustrate the preferred embodiments of the invention. They should in no way be construed, however, as limiting the broader scope of the invention.

6. EXAMPLE 1

Bcl-2 Antisense Therapy Chemosensitizes Malignant Melanoma

This example demonstrates the successful use of a bcl-2 antisense oligomer for the treatment of patients with advanced malignant melanoma. In this study, six of the patients, who were treated with the bcl-2 antisense oligomer, were systemically administered the oligomer at 5.3 or 6.5 mg/kg/day for seven days, in combination with a chemoagent. The findings reported in this Example demonstrate that, when a bcl-2 antisense oligomer is administered in high doses for short periods of time, the treatment exhibits low toxicity as scored by common toxicity criteria, reduces Bcl-2 within the tumor, facilitates apoptosis, and leads to objective tumor responses and prolonged patient survival. Included among the responding patients were several with "treatment resistant cancer" who had experienced progressive disease during treatment with standard anticancer agents, where treatment with standard agents such as dacarbazine used alone would have minimal or no expected benefit. In contrast, the combination therapy with bcl-2 antisense and dacarbazine led to unexpected durable responses and prolonged survival. Moreover, a follow-up study, which used higher doses for shorter periods in five patients, demonstrated satisfactory tolerance when the bcl-2 antisense oligomer was administered systemically at 7 mg/day for five days. Thus, the results indicate that administration of a bcl-2 antisense oligomer at high doses for a short period of time is a safe and effective therapy for melanoma. The approach outlined in this study provides a broadly applicable strategy for treating other types of cancer.

6.1. MATERIALS AND METHODS

Fourteen patients with stage 1V metastatic melanoma were eligible for this phase I/II dose escalation study if they had measurable disease, and if cutaneous metastases were accessible for biopsy and initially positive for BCL-2 expression by Western blotting (Table 1). Patients were required to have normal renal, hepatic, and hematopoietic function and no chemo- or immunotherapy four weeks prior to inclusion into the study.

BCL-2 antisense oligomer (sequence 5'TCTCCCAGCGT-GCGCCAT-3' (SEQ ID NO:17)) was administered as a continuous intravenous infusion (CIV) for 14 days by an ambulatory infusion pump (Sims Deltec Inc., St. Paul, Minn., USA) through a central venous line. Using a separate peripheral intravenous line, DTIC was administered at doses of 200 $mg/m^2$/day given by one hour infusions for 5 days on days 5 though 9 of the 14-day BCL-2 antisense oligomer therapy. Treatment cycles were repeated monthly. Dose escalation was started at 0.6 mg/kg/day and continued with 1.3, 1.7, 2.1, 3.1, 4.1, 5.3 and 6.5 mg/kg/day of BCL-2 ASO. Once safety was established in a cohort of at least 3 patients at a given dose level, new patient cohorts were entered at the next higher dose level (Waters et al., 2000, J. Clin. Oncol. 18(9):1812-23). Repeat 28 day cycles and intra-patient dose escalation were permitted in stable or responding patients after a two week observation period.

To gain clinical experience with an alternative route and schedule, six patients in the cohorts treated with 5.3 or 6.5 mg/kg/day received their first cycle by Intravenous infusion and were then switched to subcutaneous (SC) administration of BCL-2 antisense oligomer in subsequent cycles. These patients treated by the SC route received the same total daily dose, administered by twice-daily SC injections on days 1 through 7, combined with DTIC 800 $mg/m^2$ given as a one-hour infusion on day 5.

Antitumor effects were assessed after every cycle of treatment, using caliper measurement and detailed photo-documentation of patients with skin metastases; visceral metastases were documented and followed by computed tomography scans. WHO criteria were used, for classification of tumor response, requiring serial documentation lasting at least 4 weeks. Complete response was defined as disappearance of detectable metastases. Partial response was defined as a 50% or greater reduction of measurable metastases. Where patients demonstrated numerous metastases in one organ, a maximum of 5 target lesions were documented at baseline and then followed to determine response. An increase in measurable disease of more than 25%, or the appearance of new, metastatic lesions, were defined as progressive disease. In addition, a situation where target lesion diameters regressed by less than 50% but more than 25% was designated to be a minor response. All other situations were defined as stable disease. Survival was assessed from the time of first treatment on this protocol.

Toxicity was scored by common toxicity criteria, and monitored daily during drug administration, then weekly between cycles. Any treatment-related grade III or IV toxicity that would not resolve in the two weeks between treatment cycles was considered a dose limiting toxicity. Plasma samples to determine BCL-2 antisense oligomer pharmacokinetics were collected at time 0 before treatment, then on days 2, 3, 5, 6, 10, and 14 in patients receiving the two-week intravenous infusion of BCL-2 ASO; 12 hour pharmacokinetic profiles were determined in patients receiving BCL-2 antisense oligomer as subcutaneous bolus injections at the abdominal site. BCL-2 antisense oligomer plasma levels were assayed by Pharmanalyt, Baden, Austria, using HPLC (Chen et al., 1997, J. Chromatogr. B. Biomed. Sci. Appl. 692:43-51).

BCL-2 expression and apoptotic rate of melanoma metastases were assessed by Western blotting and the TUNEL method, respectively (Jansen et al., 1998, Nat. Med. 4(2):232-4). BCL-2 reductions of less than 20% compared to baseline levels were not considered to be significant due to technical limitations. Biopsied tumors were selected based on size, location, and clinical features, similar to the target lesions used for measurement of response. Excision biopsies of cutaneous melanoma metastases were performed at baseline and on day 5 of each BCL-2 antisense oligomer dose level prior to DTIC administration; additional biopsies were obtained up to cycle day 14 to document the effects of combined BCL-2 antisense oligomer and DTIC treatment. A total of 2-4 tumor biopsies per patient per dose level have been investigated. The portion of the tumor biopsy used for Western blots and TUNEL assay was also evaluated by routine histopathology to ensure consistent tumor cell content and to limit confounding effects of non-tumor cells in the biopsy sample.

6.2. RESULTS

A total of 14 patients were treated with BCL-2 antisense oligomer (0.6 to 6.5 mg/kg/day) combined with DTIC according to the two treatment regimes (I.V. or S.C.) outlined above.

BCL-2 antisense oligomer steady-state plasma levels were observed after one day of continuous intravenous infusion and increased linear with the administered dose. BCL-2 antisense oligomer doses >1.7 mg/kg/day led to consistent steady-state plasma levels over 1 µg/µl, a plasma level determined to be bioactive in animal models (Raynaud et al., 1997, J. Pharmacol. Exp. Ther. 281:420-7). At 6.5 mg/kg/day, a mean steady state plasma level of 6.47 µg/ml+/−SD=2.51 µg/ml was reached by 24 hours. BCL-2 antisense oligomer plasma levels of SC bolus injections administered twice daily were bell-shaped over 12 hours. A peak concentration of 8.6 µg/ml+/−SD=1.26 µg/ml was observed three to four hours after injection of the SC dose of 3.25 mg/kg administered at 12 h intervals. More than 90% of the 12 hour period in between subcutaneous injections, plasma levels exceeded the 1 mg/ml target plasma level, associated with biological activity. No changes in the pharmacokinetic properties were observed in patients receiving multiple cycles of therapy; concurrent DTIC treatment did not affect steady-state BCL-2 antisense oligomer plasma levels.

At baseline, BCL-2 protein expression of cutaneous melanoma metastases (Selzer et al., 1998, 8(3):197-203; Cerroni et al., 1995, Am. J. Dermatopathol. 17:7-11), was confirmed by Western blotting in all 14 patients screened for this study; serial biopsies of comparable lesions demonstrated reductions in BCL-2 protein levels during BCL-2 antisense oligomer administration (Table 1). In patient 10, serial tumor specimens were not evaluable for Western blotting due to lack of melanoma cells in the biopsy tissue. The maximal reduction of BCL-2 protein in patients treated by 14-day continuous infusion of BCL-2 antisense oligomer was typically observed by day 5 with no further decrease on day 14.83% of evaluable patients with BCL-2 antisense oligomer plasma levels exceeding 1 µg/ml (10 of 12 patients) demonstrated a clear reduction in BCL-2 expression (Table 1). Treatment cycles with BCL-2 antisense oligomer doses >1.7 mg/kg/day demonstrated a median reduction of BCL-2 protein reduction of 40% by day 5.

An increase of apoptotic cells in tumor specimen following 5 days of BCL-2 antisense oligomer treatment was observed by TUNEL staining (increase from baseline 0.85%, +/−SD=047%; to 3.17%, +/−SD=1.16%) (FIG. 2B). However, in biopsies taken after adding the apoptotic stimulus (DTIC), an additional dramatic enhancement in apoptotic cell death could be observed (FIG. 2C, 19.4%+/−SD=4.2%). The combination therapy of BCL-2 antisense oligomer and DTIC was well tolerated up to and including 6.5 mg/kg/day of BCL-2 antisense oligomer without dose-limiting toxicity (Table 2).

Hematological abnormalities were mild or moderate (grade I-III, Table 2), and followed the pattern of nadir values between treatment cycles typical for single agent DTIC. None of the patients experienced febrile neutropenia or other major clinical hematological toxicities. Grade II-III anemia requiring transfusion was observed in two patients during the study, but anemia was present at baseline in these same patients, possibly caused by prior therapies. Grade II-III lymphopenia was observed commonly, but without clinical sequelae such as unusual viral or fungal infections, or other clinical evidence for immunosuppression despite repeat cycles lasting over one year in some patients. Transient grade II-III prolongation of partial thromboplastin time was observed in three patients without clinical bleeding.

Non-hematological adverse events are listed in the lower part of Table 2. BCL-2 antisense oligomer doses over 4.1 mg/kg/day were associated with transient fever in most patients. The fever commonly reached 38° C. on days 2-3 of therapy and resolved either spontaneously or with administration of acetaminophen and continued antisense oligomer administration. At the dose levels ranging from 4.1 to 6.5 mg/kg/day, transient grade II-III elevations of transaminase and/or bilirubin were observed in 4 patients; however the causal relationship to BCL-2 antisense oligomer was not established in all patients, since two patients had hepatitis and alcoholism, respectively, and the transient liver function abnormalities were observed after DTIC, which can also lead to such laboratory changes. The liver function abnormalities typically resolved in 1 week between treatment cycles, and were not considered clinically significant or dose-limiting. Dermatological adverse events included transient rashes and urticaria, grade I in all but one patient who experienced transient grade II urticaria; these dermatological reactions responded to antihistamines and did not prevent subsequent therapy. No cumulative toxicities were observed. Some patients were treated with up to 10 cycles of therapy without requiring modifications of the planned treatment schedules.

Even though toxicity was the main endpoint of this dose escalation trial, antitumor activity was evident in 6 of 14 patients (43%, Table 1) with stage 1V melanoma, including responses seen among the 12 patients who enrolled into the study after treatment-failure of systemic melanoma therapies. 1 CR, 2 PR, and 2 MR with prolonged stabilization of disease lasting over 1 year were noted (Table 1). Clinical antitumor activity was also observed in two additional patients with stabilization of disease that was clearly progressing prior to study enrollment. Patient 12, who had bulky metastatic disease measuring over 5 cm at baseline in pelvic lymph nodes and at the site of a prior skin graft, demonstrated rapid response after 2 cycles and complete response after 4 cycles (Table 1, FIG. 3). After 4 cycles of therapy, a biopsy of the cutaneous area that had been previously positive for neoplasm showed only fibrosis with no melanoma (pathologic complete response). Patients 2 and 3 demonstrated partial response of target lesions with progression-free survivals lasting over one year. At entry to this study, patients 2 and 3 had progressive metastases despite prior treatments with carboplatin plus interferon (patient 2) and DTIC plus IL-2 (patient 3). Patients 5 and 9 both entered the study with progressive metastatic disease despite systemic therapy with DTIC+ interferon or interferon alone, and developed minor responses under BCL-2 antisense plus DTIC therapy. The estimated median survival exceeds at least one year in all patients.

6.3 CONCLUSION

This report demonstrates the safety and feasibility of treatment with an antisense drug combined with chemotherapy in cancer patients. BCL-2 antisense oligomer treatment was well tolerated, reduced the target protein within the tumor, facilitated apoptosis, and led to objective tumor responses with prolonged survival also in patients who entered the study after treatment failure of other therapies (Table 1).

The primary aim of the present study was to determine the toxicity of BCL-2 antisense oligomer combined with DTIC therapy. Concerning the non-hematological side effects (Table 2), up to and including BCL-2 antisense oligomer dose levels of 3.1 mg/kg/day, no side effects other than those reported for single agent DTIC therapy were noted in this study. With BCL-2 antisense oligomer doses at and above 4.1 mg/kg/day in combination with DTIC, transient grade II-III elevations of transaminase and/or bilirubin were observed (Table 2). In this study, the liver function abnormalities were not dose-limiting nor associated with adverse clinical sequelae. Non-dose-limiting changes of αPTT were noted at and above daily BCL-2 antisense oligomer doses of 5.3 mg/kg.

Lymphopenia was also the most frequent hematological side effect observed in this study. The lymphopenia was not clinically significant, and there were no unusual infections in patients treated with cyclic therapy and followed over one year. In contrast, some levels of thrombocytopenia have been observed with multiple phosphorothioate antisense drugs, and this toxicity was dose limiting in the study of BCL-2 antisense oligomer in patients with NHL (Waters et al., 2000, J. Clin. Oncol. 18(9):1812-23). Even though this study combined BCL-2 antisense oligomer with chemotherapy, leading to transient myelo-suppression after the DTIC, and steady-state plasma levels exceeded those reported in the NHL study, we did not observe dose-limiting thrombocytopenia. In summary, neither overlapping nor cumulative dose-limiting toxicities between DTIC and BCL-2 antisense oligomer were observed in this patient population.

Our data demonstrate that the biologically relevant steady-state plasma levels (>1 ug/ml) can be easily achieved with BCL-2 antisense oligomer doses of about 2 mg/kg/day, and the maximal tolerated dose has not been reached in combination with DTIC chemotherapy.

In a recent follow-up to the treatment regimens investigated in this trial, BCL-2 antisense oligomer administered intravenously by infusion (7 mg/kg/day) over 5 days has been administered to an expanded cohort (5 patients) prior to DTIC 1000 mg/m$^2$ in each 21-day cycle, and demonstrated satisfactory tolerance.

The results therefore indicate that BCL-2 antisense oligomer can be administered safely in combination with an anticancer drug to treat cancer in the clinical setting. The results differ from prior published data showing biologic activity and clinical responses with a 14-day infusion given only by a continuous subcutaneous infusion (Waters et al., 2000, J. Clin. Oncol. 18(9):1812-23), since the results described herein demonstrate that multiple routes (intravenous infusion, multiple daily subcutaneous injections) and shorter schedules of administration of 5-7 days can also lead to biologic activity of G3139 and clinical responses. In responding patients, the initial antitumor activity was seen rapidly within 2-3 cycles. The majority of patients entered the study with progressive metastatic disease after treatment failure of DTIC-containing regimens or after other standard treatments for metastatic melanoma. Nevertheless, antitumor responses were noted in 6 of 14 patients (43%), and in two additional patients, a stabilization of the disease was observed. The estimated median survival of all patients exceeds 12 months. These initial results compare favorably to negligible response rates and median survival times of about 4 to 5 months observed in patients with advanced melanoma after treatment failure of first-line systemic therapy.

TABLE 1

Study Synopsis

| Patient No. | Age/ Sex | Date of First Diagnosis | Melanoma Metastases | Tumor Stage | Prior Therapy | BCL-2 ASO (mg/kg/d) | Max. % BCL-2 Reduction | Response | Survival (Months) |
|---|---|---|---|---|---|---|---|---|---|
| 1 | 49/F | August 1995 | LNN, Skin | IV | DTIC, IF, RT, HEP | 0.6 | 0 | PD | 6,6 |
| 2* | 41/F | March 1995 | Skin | IV | CP, IFN-α, RT, HEP | 0.6-6.5 | 40 | PR | 20,5 |
| 3* | 69/M | June 1994 | LNN, Skin | IV | DTIC, IL-2, GM-CSF | 0.6-6.5 | 40 | PR | 23,3[+] |
| 4 | 52/M | May 1998 | LNN, Skin | IV | DTIC, IFN-α | 0.6-4.1 | 35 | MR | 13,7 |
| 5 | 63/F | January 1992 | Skin | IV | DTIC, IFN-α | 3.1-4.1 | 20 | MR | 5,1 |
| 6 | 56/M | August 1996 | Lung, Skin | IV | DTIC, IFN-α | 3.1-5.3 | 60 | PD | 2,4 |
| 7 | 61/F | May 1997 | Lung, Liver, Skin | IV | DTIC, FOT | 4.1 | 20 | PD | 7,1 |
| 8* | 60/F | March 1995 | Skin | IV | IFN-α, RT | 5.3-6.5 | 60 | Stable | 15,3[+] |
| 9* | 75/F | June 1998 | LNN, Skin | IV | IFN-α | 5.3-6.5 | 60 | MR | 15,3[+] |
| 10 | 44/F | April 1986 | LNN, Skin | IV | IFN-α | 6.5 | N.A. | PD | 14,4[+] |
| 11 | 63/M | April 1997 | Lung, Skin | IV | IFN-α, CP, CIS | 6.5 | 0 | PD | 12,5[+] |
| 12* | 90/F | July 1994 | LNN, Skin | IV | None | 6.5 | 70 | CR | 12,5[+] |
| 13* | 67/M | June 1996 | Lung, Skin | IV | None | 6.5 | 0 | PD | 1,1 |
| 14 | 76/M | April 1999 | Lung, Skin | IV | IFN-α | 6.5 | 40 | Stable | 7,8 |

CP = Carboplatin;
CIS = Cisplatin;
FOT = Fotemustine;
HEP = hyperthermic extremity perfusion;
IFN-α = interferon-α;
NA = not applicable;
RT = radiation therapy.
A total number of 47 cycles of BCL-2 ASO plus DTIC have been administered.
*Patients who also received BCL-2 ASO subcutaneously with doses of 5.3 and 6.5 mg/kg/day, administered after initial intravenous treatment cycles.
[+]Observation period continues.

TABLE 2

Adverse Events During Treatment

| | Common toxicity criteria grade No. Patients | | | | |
|---|---|---|---|---|---|
| | 0 | 1 | 2 | 3 | 4 |
| Hematological events | | | | | |
| Anemia | 12 | | | 2 | |
| Leucopenia | 7 | 2 | 3 | 2 | |
| Neutropenia | 10 | 2 | 2 | | |
| Lymphopenia | 1 | 1 | 7 | 5 | |
| Thrombocytopenia | 8 | 4 | 2 | | |
| Coagulation | 3 | 8 | 2 | 1 | |
| Non-hematological events | | | | | |
| Cardiovascular | 14 | | | | |
| Pulmonary | 14 | | | | |
| Renal | 14 | | | | |
| Gastrointestinal | 9 | 5 | | | |
| Liver (SGOT, Bilirubin) | 1 | 7 | 2 | 4 | |
| Neurological (Headache) | 11 | 3 | | | |
| Dermatological | 9 | 4 | 1 | | |
| Fever | 7 | 1 | 6 | | |

Events are listed irrespective of causal relationship to BCL-2 ASO therapy

7. EXAMPLE 2

A Phase I, Pharmacokinetic and Biologic Correlative Study of G3139 (bcl-2 Antisense Oligonucleotide) and Docetaxel in Patients with Hormone-Refractory Prostate Cancer This example demonstrates the successful use of a bcl-2 antisense oligomer for the treatment of patients with hormone-refractory prostate cancer, which is resistant to androgen ablation therapy and cytotoxic chemotherapy. The bcl-2 antisense oligomer was systemically administered at 5 to 7 mg/kg/day for five days, in combination with a chemoagent. This study reports that two patients, who were treated with the bcl-2 antisense oligomer and a chemoagent, demonstrated responses to the treatment. The findings reported in this Example demonstrate that, when a bcl-2 antisense oligomer is administered in high doses for short periods of time, the treatment exhibits low toxicity while demonstrating objective clinical responses. The approach outlined in this study provides a broadly applicable strategy for treating other types of cancer.

7.1. MATERIALS AND METHODS

In this study, G3139 was administered as a continuous intravenous infusion for five days per cycle on treatment cycle days 1-6, followed by docetaxel administered intravenously on day 6. Courses were repeated every 21 days. Eleven patients with hormone-refractory prostate cancer received therapy at three dose levels ranging from G3139 at 5 mg/kg/day with 60 mg/m$^2$ docetaxel to G3139 at 7 mg/kg/day followed by 75 mg/m$^2$ docetaxel.

7.2. RESULTS

Major toxicities were similar to docetaxel alone. One heavily pretreated patient had prolonged (>5 days) uncomplicated grade 4 neutropenia. Other toxicities include grade 1 stomatitis in three patients, and febrile neutropenia during course 2 in one patient. Preliminary pharmacokinetic results (HPLC) demonstrate mean G3139 steady-state plasma concentrations of 3.09 μg/mL at the 5 mg/kg/day dose level. Preliminary flow cytometric and western blot analysis indicated >50% downregulation of Bcl-2 protein by day 6 in peripheral blood mononuclear cells prior to docetaxel treatment. Prostate-specific antigen and symptomatic responses were observed in 2 of 3 evaluable taxane-naive patients, including a nine-fold reduction in prostate-specific antigen durable for greater than cycles.

7.3. CONCLUSION

G3139 can be safely administered in combination with docetaxel, and as these results demonstrate, the combination has significant therapeutic effects in the treatment of cancer. The results differ from prior published data showing biologic activity and clinical responses with a 14-day infusion given only by a continuous subcutaneous infusion (Waters et al., 2000, J. Clin. Oncol. 18(9):1812-23), since the results described herein demonstrate that shorter schedules of administration (5 days) given by an alternative route (intravenously) can also lead to biologic activity of G3139 and clinical responses. G3139 treatment is biologically active within five days of administration, demonstrated by effective downregulation of Bcl-2 protein in peripheral blood mononuclear cells, and has encouraging preliminary antitumor activity in hormone-refractory prostate cancer patients.

8. EXAMPLE 3

Phase I Trial of Genasense™ (G3139), a Bcl-2 Antisense, in Refractory or Relapsed Acute Leukemia This example demonstrates the successful use of a bcl-2 antisense oligomer for the treatment of patients with acute leukemia. The bcl-2 antisense oligomer was systemically administered at 4 mg/kg/day for ten days, in combination with two chemoagents. This study reports that five of ten patients, who were treated with the bcl-2 antisense oligomer and a chemoagent, demonstrated responses to the treatment. Moreover, responses were also noted in patients which were administered fludarabine and cytosine arabinoside, at doses lower than the standard doses normally used for treatment of leukemia or other cancers. The findings reported in this Example demonstrate that objective clinical responses can be obtained when a bcl-2 antisense oligomer is administered for a short period of time.

8.1. MATERIALS AND METHODS

G3139 (4 mg/kg/day) was given to patients (ten patients in total) on days 1-10, whereas fludarabine (starting at a reduced dose of 15 mg/m$^2$), cytosine arabinoside (Ara-C) (starting at a reduced dose of 1000 mg/m$^2$) and G-CSF (FLAG) are given on days 6-10 of the treatment cycle, and escalated in successive cohorts. The normal FLAG combination regimen includes two-fold higher doses of fludarabine and Ara-C than the doses used in this study.

| Pts age/ sex | Dx & Status Pre-G3139 | Time to REL(m)[1] | Previous Regimens | Previous HDAC[2] | Response | Disease status (d)[3] |
|---|---|---|---|---|---|---|
| 69/F | primary REF ALL | NA[4] | 1 | No | CR[5] | NED[8] (53) |
| 55/F | primary REF AML | NA | 3 | Yes | CR | REL (142) |
| 57/M | 2$^{nd}$ REL AML | 12 | 2 | Yes | CR | NED (111) |

-continued

| Pts age/sex | Dx & Status Pre-G3139 | Time to REL(m)[1] | Previous Regimens | Previous HDAC[2] | Response | Disease status (d)[3] |
|---|---|---|---|---|---|---|
| 23/M | 1st REL AML | 3 | 1 | Yes | PR[6] | REL (83) |
| 61/F | 1st REL AML | 7 | 1 | No | PR | NED (76) |
| 54/M | primary REF AML | NA | 1 | No | NR[7] | REF |
| 61/F | 1st REL AML | 6 | 2 | No | NR | REF |
| 73/F | 2nd REL AML | 8 | 2 | Yes | NR | REF |
| 39/M | 2nd REL AML | 3 | 2 | Yes | NR | REF |
| 55/F | 2nd REL AML | 6 | 3 | Yes | NR | REF |

[1](m), months from CR;
[2]high-dose Ara-C;
[3](d), days from G3139 start;
[4]NA, not applicable;
[5]CR, complete response;
[6]PR, partial response;
[7]NR, no response;
[8]NED, no evidence of disease;
REF, refractory;
REL, relapsed.

8.2. RESULTS

Therapy-related fever, nausea, emesis, hypocalcemia, hypophosphatemia, and fluid retention were not dose-limiting. Hematologic toxicities were as expected. Steady state G3139 plasma levels exceeding the relevant target level (1 µg/ml) were achieved after 24 h. Three patients achieved complete response and received a second course of therapy; two continued with no evidence of disease at day 53 and day 111. Two patients had no evidence of disease but persistent neutropenia/thrombocytopenia at day 52 and day 55; one of them continues with no evidence of disease at day 76. Three of five responders had prior treatment with high-dose Ara-C, and therefore, documenting a major response to another Ara-C combination program, as described in this study, especially using lower doses than those used in regimens of the prior treatments, was unexpected.

8.3. CONCLUSION

The results indicate that G3139 is feasible for addition to multi-cycle induction regimens for acute leukemia, which in this study demonstrated 50% response rate, including patients with refractory acute leukemia and prior treatment with high-dose Ara-C. Major responses were also observed using lower-than-normal dose levels of fludarabine and Ara-C when combined with a bcl-2 antisense regimen.

All references cited herein are specifically incorporated by reference as if fully set forth herein.

Having hereinabove disclosed exemplary embodiments of the present invention, those skilled in the art will recognize that this disclosure is only exemplary such that various alternatives, adaptations, and modifications are within the scope of the invention, and are contemplated by the Applicants. Accordingly, the present invention is not limited to the specific embodiments as illustrated above, but is defined by the following claims.

We claim:

1. A method of treating cancer in a human comprising administering to said human, in which such treatment is desired, a bcl-2 antisense oligonucleotide at a dose of 0.01 to 50 mg/kg daily in more than one cycle of therapy, each cycle of therapy consisting of 3 to 9 days, wherein each cycle of therapy is separated by an interval of time wherein said human receives no bcl-2 antisense oligonucleotide, and wherein said interval of time comprises at least one day, and further comprising administering one or more cancer therapeutics.

2. The method of claim 1, wherein each cycle of therapy consists of 4 to 7 days.

3. The method of claim 1 wherein administration of the cancer therapeutic follows administration of the bcl-2 antisense oligonucleotide.

4. The method of claim 1 wherein administration of the cancer therapeutic precedes administration of the bcl-2 antisense oligonucleotide.

5. The method of claim 1 wherein the cancer therapeutic is administered concurrently with the bcl-2 antisense oligonucleotide.

6. The method of claim 1 wherein said cancer therapeutic is a chemoagent, radiotherapeutic, immunotherapeutic, cancer vaccine, anti-angiogenic agent, cytokine, gene therapeutic, or hormonal agent.

7. The method of claim 6, wherein said cancer therapeutic is a chemoagent, and wherein said chemoagent is dacarbazine, docetaxel, paclitaxel, cisplatin, 5-fluorouracil, doxorubicin, etoposide, cyclophosphamide, fludarabine, irinotecan or cytosine arabinoside (Ara-C).

8. The method as in any of claims 1 or claim 6 wherein said cancer therapeutic is administered at a dose which is below the effective dose when the cancer therapeutic is administered without the bcl-2 antisense oligonucleotide.

9. The method as in any of claims 1 or 2, wherein said administration is by oral, intravenous infusion, subcutaneous injection, intramuscular injection, topical, depo injection, implantation, time-release mode, intracavitary, intranasal, inhalation, intratumor, or intraocular administration.

10. The method as in any of claims 1 or 2, wherein said cancer is a cancer of the hematopoietic system, skin, bone and soft tissue, reproductive system, genitourinary system, breast, endocrine system, brain, central nervous system, peripheral nervous system, kidney, lung, respiratory system, thorax, gastrointestinal and alimentary canal, lymph nodes, pancreas, hepatobiliary system, or cancer of unknown primary site.

11. The method of any of claims 1 or 2, wherein said cancer is non-Hodgkin's lymphoma, Hodgkin's lymphoma, leukemia, colon carcinoma, rectal carcinoma, pancreatic cancer, breast cancer, ovarian cancer, prostate cancer, renal cell carcinoma, heptoma, bile duct carcinoma, choriocarcinoma, cervical cancer, testicular cancer, lung carcinoma, bladder carcinoma, melanoma, head and neck cancer or brain cancer.

12. The method as in any of claim 1 or 2, wherein the antisense oligonucleotide is from 10 to 40 bases in length and is complementary to the pre-mRNA or mRNA of the bcl-2 gene.

13. The method of claim 12, wherein the antisense oligonucleotide comprises at least two phosphorothioate linkages.

14. The method of claim 13, wherein the antisense oligonucleotide comprises the sequence TCTCCCAGCGTGCGCCAT (SEQ ID NO: 17).

* * * * *

UNITED STATES PATENT AND TRADEMARK OFFICE
CERTIFICATE OF CORRECTION

| | | |
|---|---|---|
| PATENT NO. | : 7,795,232 B1 | Page 1 of 1 |
| APPLICATION NO. | : 09/709170 | |
| DATED | : September 14, 2010 | |
| INVENTOR(S) | : Raymond P. Warrell et al. | |

It is certified that error appears in the above-identified patent and that said Letters Patent is hereby corrected as shown below:

Claim 1, lines 53-54, "a dose of 0.01 to 50", should read -- a dose of 5 to 7 --.

Signed and Sealed this

Ninth Day of November, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,795,232 B1 |
| APPLICATION NO. | : 09/709170 |
| DATED | : September 14, 2010 |
| INVENTOR(S) | : Raymond P. Warrell et al. |

It is certified that error appears in the above-identified patent and that said Letters Patent is hereby corrected as shown below:

Claim 1, Column 35, lines 53-54, "a dose of 0.01 to 50", should read -- a dose of 5 to 7 --.

This certificate supersedes the Certificate of Correction issued November 9, 2010.

Signed and Sealed this

Fourteenth Day of December, 2010

David J. Kappos
*Director of the United States Patent and Trademark Office*

SEQUENCE LISTING

```
<160> NUMBER OF SEQ ID NOS: 17

<210> SEQ ID NO 1
<211> LENGTH: 20
<212> TYPE: DNA
<213> ORGANISM: Homo Sapiens

<400> SEQUENCE: 1
cagcgtgcgc catccttccc                                              20

<210> SEQ ID NO 2
<211> LENGTH: 35
<212> TYPE: DNA
<213> ORGANISM: Homo Sapiens

<400> SEQUENCE: 2
cttttcctct gggaaggatg gcgcacgctg ggaga                             35

<210> SEQ ID NO 3
<211> LENGTH: 20
<212> TYPE: DNA
<213> ORGANISM: Homo Sapiens

<400> SEQUENCE: 3
gatgcaccta cccagcctcc                                              20

<210> SEQ ID NO 4
<211> LENGTH: 33
<212> TYPE: DNA
<213> ORGANISM: Homo Sapiens
```

```
<400> SEQUENCE: 4
acggggtacg gaggctgggt aggtgcatct ggt                                    33

<210> SEQ ID NO 5
<211> LENGTH: 20
<212> TYPE: DNA
<213> ORGANISM: Homo Sapiens

<400> SEQUENCE: 5
acaaaggcat cctgcagttg                                                   20

<210> SEQ ID NO 6
<211> LENGTH: 36
<212> TYPE: DNA
<213> ORGANISM: Homo Sapiens

<400> SEQUENCE: 6
cccccaactg caggatgcct ttgtggaact gtacgg                                 36

<210> SEQ ID NO 7
<211> LENGTH: 20
<212> TYPE: DNA
<213> ORGANISM: Homo Sapiens

<400> SEQUENCE: 7
gggaaggatg gcgcacgctg                                                   20

<210> SEQ ID NO 8
<211> LENGTH: 17
<212> TYPE: DNA
<213> ORGANISM: Homo Sapiens

<400> SEQUENCE: 8
cgcgtgcgac cctcttg                                                      17

<210> SEQ ID NO 9
<211> LENGTH: 17
<212> TYPE: DNA
<213> ORGANISM: Homo Sapiens

<400> SEQUENCE: 9
taccgcgtgc gaccctc                                                      17

<210> SEQ ID NO 10
<211> LENGTH: 17
<212> TYPE: DNA
<213> ORGANISM: Homo Sapiens

<400> SEQUENCE: 10
tcctaccgcg tgcgacc                                                      17

<210> SEQ ID NO 11
<211> LENGTH: 17
<212> TYPE: DNA
<213> ORGANISM: Homo Sapiens

<400> SEQUENCE: 11
ccttcctacc gcgtgcg                                                      17

<210> SEQ ID NO 12
<211> LENGTH: 17
<212> TYPE: DNA
```

```
<213> ORGANISM: Homo Sapiens

<400> SEQUENCE: 12
gacccttcct accgcgt                                                  17

<210> SEQ ID NO 13
<211> LENGTH: 17
<212> TYPE: DNA
<213> ORGANISM: Homo Sapiens

<400> SEQUENCE: 13
ggagaccctt cctaccg                                                  17

<210> SEQ ID NO 14
<211> LENGTH: 15
<212> TYPE: DNA
<213> ORGANISM: Homo Sapiens

<400> SEQUENCE: 14
gcggcggcag cgcgg                                                    15

<210> SEQ ID NO 15
<211> LENGTH: 15
<212> TYPE: DNA
<213> ORGANISM: Homo Sapiens

<400> SEQUENCE: 15
cggcggggcg acgga                                                    15

<210> SEQ ID NO 16
<211> LENGTH: 16
<212> TYPE: DNA
<213> ORGANISM: Homo Sapiens

<400> SEQUENCE: 16
cgggagcgcg gcgggc                                                   16

<210> SEQ ID NO 17
<211> LENGTH: 18
<212> TYPE: DNA
<213> ORGANISM: Homo Sapiens

<400> SEQUENCE: 17
tctcccagcg tgcgccat                                                 18
```